(12) United States Patent
Montorfano et al.

(10) Patent No.: US 11,931,252 B2
(45) Date of Patent: Mar. 19, 2024

(54) DISK-BASED VALVE APPARATUS AND METHOD FOR THE TREATMENT OF VALVE DYSFUNCTION

(71) Applicant: Cephea Valve Technologies, Inc., San Jose, CA (US)

(72) Inventors: Matteo Montorfano, Milan (IT); Alaide Chieffo, Milan (IT); Juan F. Granada, Upper Saddle River, NJ (US)

(73) Assignee: Cephea Valve Technologies, Inc., Abbott Park, IL (US)

( * ) Notice: Subject to any disclaimer, the term of this patent is extended or adjusted under 35 U.S.C. 154(b) by 331 days.

(21) Appl. No.: 16/511,235

(22) Filed: Jul. 15, 2019

(65) Prior Publication Data

US 2019/0336287 A1 Nov. 7, 2019

Related U.S. Application Data

(60) Continuation of application No. 14/281,714, filed on May 19, 2014, now Pat. No. 10,456,255, which is a (Continued)

(51) Int. Cl.
*A61F 2/24* (2006.01)

(52) U.S. Cl.
CPC .......... *A61F 2/2409* (2013.01); *A61F 2/2418* (2013.01); *A61F 2/2445* (2013.01); (Continued)

(58) Field of Classification Search
CPC ........ A61F 2/24; A61F 2/2409; A61F 2/2418; A61F 2/2433
See application file for complete search history.

(56) References Cited

U.S. PATENT DOCUMENTS

| 3,334,629 A | 8/1967 | Cohn |
| 3,409,013 A | 11/1968 | Berry |

(Continued)

FOREIGN PATENT DOCUMENTS

| CA | 2859666 A1 | 6/2013 |
| CN | 1338951 A | 3/2002 |

(Continued)

OTHER PUBLICATIONS

Andersen et al.; Transluminal implantation of artificial heart valves. Description of a new expandable aortic valve and initial results with implantation by catheter technique in closed chest pigs; Euro. Heart J.; 13(5): 704-708; May 1992.

(Continued)

*Primary Examiner* — Seema Mathew
(74) *Attorney, Agent, or Firm* — SLEMAN & LUND LLP

(57) ABSTRACT

The present invention comprises a novel and safer mechanism of deployment using a self-positioning, self-centering, and self-anchoring method. To embody the present invention, a disk-based valve apparatus allowing the repositioning and retrieval of the implantable valve while working on a dysfunctional valve structure is disclosed. The disk-based valve apparatus may comprise one or more disks, either proximal or distal, a valve-housing component and a valve component. The one or more disks may be either proximal or distal, may be either connected to each other or disconnected from each other and may either be symmetrical or have different shapes and dimensions. The disk-based valve apparatus may be self anchoring, such as anchored by pressure from the one or more disk, or may be anchored using any anchoring.

7 Claims, 9 Drawing Sheets

Related U.S. Application Data division of application No. 14/033,185, filed on Sep. 20, 2013, now Pat. No. 8,728,155, which is a continuation of application No. PCT/IB2012/000563, filed on Mar. 21, 2012.

(60) Provisional application No. 61/454,703, filed on Mar. 21, 2011.

(52) U.S. Cl.
CPC .  *A61F 2230/005* (2013.01); *A61F 2230/0058* (2013.01); *A61F 2230/0065* (2013.01); *A61F 2230/0078* (2013.01); *A61F 2250/0039* (2013.01)

(56) References Cited

U.S. PATENT DOCUMENTS

| | | |
|---|---|---|
| 3,540,431 A | 11/1970 | Mobin-Ubdin |
| 3,628,535 A | 12/1971 | Ostrowsky et al. |
| 3,642,004 A | 2/1972 | Osthagen et al. |
| 3,657,744 A | 4/1972 | Ersek |
| 3,671,979 A | 6/1972 | Moulopoulos |
| 3,714,671 A | 2/1973 | Goodenough |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 4,056,854 A | 11/1977 | Boretos et al. |
| 4,106,129 A | 8/1978 | Carpentier et al. |
| 4,233,690 A | 11/1980 | Akins |
| 4,291,420 A | 9/1981 | Reul |
| 4,326,306 A | 4/1982 | Poler |
| 4,423,809 A | 1/1984 | Mazzocco |
| 4,425,908 A | 1/1984 | Simon |
| 4,501,030 A | 2/1985 | Lane |
| 4,531,943 A | 7/1985 | Van Tassel et al. |
| 4,580,568 A | 4/1986 | Gianturco |
| 4,602,911 A | 7/1986 | Ahmadi et al. |
| 4,610,688 A | 9/1986 | Silvestrini et al. |
| 4,617,932 A | 10/1986 | Kornberg |
| 4,648,881 A | 3/1987 | Carpentier et al. |
| 4,655,218 A | 4/1987 | Kulik et al. |
| 4,655,771 A | 4/1987 | Wallsten |
| 4,662,885 A | 5/1987 | DiPisa, Jr. |
| 4,665,906 A | 5/1987 | Jervis |
| 4,710,192 A | 12/1987 | Liotta et al. |
| 4,733,665 A | 3/1988 | Palmaz |
| 4,755,181 A | 7/1988 | Goe |
| 4,796,629 A | 1/1989 | Grayzel |
| 4,819,751 A | 4/1989 | Shimada et al. |
| 4,834,755 A | 5/1989 | Silvestrini et al. |
| 4,856,516 A | 8/1989 | Hillstead |
| 4,865,600 A | 9/1989 | Carpentier et al. |
| 4,872,874 A | 10/1989 | Taheri |
| 4,873,978 A | 10/1989 | Ginsburg |
| 4,909,252 A | 3/1990 | Goldberger |
| 4,917,102 A | 4/1990 | Miller et al. |
| 4,927,426 A | 5/1990 | Dretler |
| 4,986,830 A | 1/1991 | Owens et al. |
| 4,994,077 A | 2/1991 | Dobben |
| 5,002,556 A | 3/1991 | Ishida et al. |
| 5,002,559 A | 3/1991 | Tower |
| 5,064,435 A | 11/1991 | Porter |
| 5,161,547 A | 11/1992 | Tower |
| 5,163,953 A | 11/1992 | Vince |
| 5,209,741 A | 5/1993 | Spaeth |
| 5,258,023 A | 11/1993 | Reger |
| 5,258,042 A | 11/1993 | Mehta |
| 5,332,402 A | 7/1994 | Teitelbaum |
| 5,336,258 A | 8/1994 | Quintero et al. |
| 5,350,398 A | 9/1994 | Pavcnik et al. |
| 5,370,685 A | 12/1994 | Stevens |
| 5,389,106 A | 2/1995 | Tower |
| 5,397,351 A | 3/1995 | Pavcnik et al. |
| 5,405,377 A | 4/1995 | Cragg |
| 5,411,552 A | 5/1995 | Andersen et al. |
| 5,425,762 A | 6/1995 | Muller |
| 5,431,676 A | 7/1995 | Dubrul et al. |
| 5,443,495 A | 8/1995 | Buscemi et al. |
| 5,443,499 A | 8/1995 | Schmitt |
| 5,476,506 A | 12/1995 | Lunn |
| 5,476,510 A | 12/1995 | Eberhardt et al. |
| 5,480,423 A | 1/1996 | Ravenscroft et al. |
| 5,507,767 A | 4/1996 | Maeda et al. |
| 5,534,007 A | 7/1996 | St. Germain et al. |
| 5,545,133 A | 8/1996 | Burns et al. |
| 5,545,211 A | 8/1996 | An et al. |
| 5,549,665 A | 8/1996 | Vesely et al. |
| 5,554,183 A | 9/1996 | Nazari |
| 5,554,185 A | 9/1996 | Block et al. |
| 5,571,215 A | 11/1996 | Sterman et al. |
| 5,573,520 A | 11/1996 | Schwartz et al. |
| 5,575,818 A | 11/1996 | Pinchuk |
| 5,645,559 A | 7/1997 | Hachtman et al. |
| 5,662,671 A | 9/1997 | Barbut et al. |
| 5,667,523 A | 9/1997 | Bynon et al. |
| 5,674,277 A | 10/1997 | Freitag |
| 5,693,083 A | 12/1997 | Baker et al. |
| 5,695,498 A | 12/1997 | Tower |
| 5,713,953 A | 2/1998 | Vallana et al. |
| 5,716,370 A | 2/1998 | Williamson, IV et al. |
| 5,720,391 A | 2/1998 | Dohm et al. |
| 5,725,552 A | 3/1998 | Kotula |
| 5,733,325 A | 3/1998 | Robinson et al. |
| 5,735,842 A | 4/1998 | Krueger et al. |
| 5,769,812 A | 6/1998 | Stevens et al. |
| 5,807,405 A | 9/1998 | Vanney et al. |
| 5,817,126 A | 10/1998 | Imran |
| 5,824,041 A | 10/1998 | Lenker et al. |
| 5,824,043 A | 10/1998 | Cottone, Jr. |
| 5,824,053 A | 10/1998 | Khosravi et al. |
| 5,824,055 A | 10/1998 | Spiridigliozzi et al. |
| 5,824,056 A | 10/1998 | Rosenberg |
| 5,824,064 A | 10/1998 | Taheri |
| 5,843,158 A | 12/1998 | Lenker et al. |
| 5,855,597 A | 1/1999 | Jayaraman |
| 5,855,601 A | 1/1999 | Bessler et al. |
| 5,860,966 A | 1/1999 | Tower |
| 5,861,024 A | 1/1999 | Rashidi |
| 5,861,028 A | 1/1999 | Angell |
| 5,868,783 A | 2/1999 | Tower |
| 5,876,448 A | 3/1999 | Thompson et al. |
| 5,885,228 A | 3/1999 | Rosenman et al. |
| 5,888,201 A | 3/1999 | Stinson et al. |
| 5,891,191 A | 4/1999 | Stinson |
| 5,895,399 A | 4/1999 | Barbut et al. |
| 5,907,893 A | 6/1999 | Zadno-Azizi et al. |
| 5,911,734 A | 6/1999 | Tsugita et al. |
| 5,925,063 A | 7/1999 | Khosravi |
| 5,944,738 A | 8/1999 | Amplatz et al. |
| 5,954,766 A | 9/1999 | Zadno-Azizi et al. |
| 5,957,949 A | 9/1999 | Leonhardt et al. |
| 5,957,973 A | 9/1999 | Quiachon |
| 5,968,070 A | 10/1999 | Bley et al. |
| 5,984,957 A | 11/1999 | Laptewicz, Jr. et al. |
| 5,984,959 A | 11/1999 | Robertson et al. |
| 5,984,973 A | 11/1999 | Girard |
| 5,993,469 A | 11/1999 | McKenzie et al. |
| 5,997,557 A | 12/1999 | Barbut et al. |
| 6,010,522 A | 1/2000 | Barbut et al. |
| 6,022,370 A | 2/2000 | Tower |
| 6,027,525 A | 2/2000 | Suh et al. |
| 6,042,598 A | 3/2000 | Tsugita et al. |
| 6,042,607 A | 3/2000 | Williamson, IV et al. |
| 6,093,203 A | 7/2000 | Uflacker |
| 6,113,612 A | 9/2000 | Swanson |
| 6,123,723 A | 9/2000 | Konya et al. |
| 6,142,987 A | 11/2000 | Tsugita |
| 6,162,245 A | 12/2000 | Jayaraman |
| 6,165,209 A | 12/2000 | Patterson et al. |
| 6,168,579 B1 | 1/2001 | Tsugita |
| 6,171,327 B1 | 1/2001 | Daniel et al. |
| 6,174,322 B1 | 1/2001 | Schneidt |

(56) References Cited

U.S. PATENT DOCUMENTS

| | | |
|---|---|---|
| 6,179,859 B1 | 1/2001 | Bates et al. |
| 6,187,016 B1 | 2/2001 | Hedges et al. |
| 6,197,053 B1 | 3/2001 | Cosgrove et al. |
| 6,200,336 B1 | 3/2001 | Pavcnik et al. |
| 6,206,909 B1 | 3/2001 | Hanada et al. |
| 6,214,036 B1 | 4/2001 | Letendre et al. |
| 6,221,006 B1 | 4/2001 | Dubrul et al. |
| 6,221,096 B1 | 4/2001 | Aiba et al. |
| 6,231,544 B1 | 5/2001 | Tsugita et al. |
| 6,231,551 B1 | 5/2001 | Barbut |
| 6,241,757 B1 | 6/2001 | An et al. |
| 6,245,102 B1 | 6/2001 | Jayaraman |
| 6,251,135 B1 | 6/2001 | Stinson et al. |
| 6,258,114 B1 | 7/2001 | Konya et al. |
| 6,258,115 B1 | 7/2001 | Dubrul |
| 6,258,120 B1 | 7/2001 | McKenzie et al. |
| 6,277,555 B1 | 8/2001 | Duran et al. |
| 6,309,417 B1 | 10/2001 | Spence et al. |
| 6,312,465 B1 | 11/2001 | Griffin |
| 6,319,281 B1 | 11/2001 | Patel |
| 6,336,934 B1 | 1/2002 | Gilson et al. |
| 6,336,937 B1 | 1/2002 | Vonesh et al. |
| 6,338,735 B1 | 1/2002 | Stevens |
| 6,348,063 B1 | 2/2002 | Yassour et al. |
| 6,352,708 B1 | 3/2002 | Duran et al. |
| 6,361,545 B1 | 3/2002 | Macoviak et al. |
| 6,371,970 B1 | 4/2002 | Khosravi et al. |
| 6,371,983 B1 | 4/2002 | Lane |
| 6,379,368 B1 | 4/2002 | Corcoran et al. |
| 6,379,383 B1 | 4/2002 | Palmaz et al. |
| 6,398,807 B1 | 6/2002 | Chouinard et al. |
| 6,409,750 B1 | 6/2002 | Hyodoh et al. |
| 6,411,552 B1 | 6/2002 | Chiba |
| 6,416,510 B1 | 7/2002 | Altman et al. |
| 6,419,696 B1 | 7/2002 | Ortiz et al. |
| 6,425,916 B1 | 7/2002 | Garrison et al. |
| 6,440,152 B1 | 8/2002 | Gainor |
| 6,440,164 B1 | 8/2002 | DiMatteo et al. |
| 6,454,799 B1 | 9/2002 | Schreck |
| 6,458,153 B1 | 10/2002 | Bailey et al. |
| 6,468,303 B1 | 10/2002 | Amplatz et al. |
| 6,475,239 B1 | 11/2002 | Campbell et al. |
| 6,482,228 B1 | 11/2002 | Norred |
| 6,485,502 B2 | 11/2002 | Don Michael et al. |
| 6,494,909 B2 | 12/2002 | Greenhalgh |
| 6,503,272 B2 | 1/2003 | Duerig et al. |
| 6,527,800 B1 | 3/2003 | McGuckin, Jr. et al. |
| 6,540,768 B1 | 4/2003 | Diaz et al. |
| 6,562,058 B2 | 5/2003 | Seguin et al. |
| 6,592,546 B1 | 7/2003 | Barbut et al. |
| 6,592,614 B2 | 7/2003 | Lenker et al. |
| 6,610,077 B1 | 8/2003 | Hancock et al. |
| 6,616,675 B1 | 9/2003 | Evard et al. |
| 6,616,682 B2 | 9/2003 | Joergensen et al. |
| 6,622,604 B1 | 9/2003 | Chouinard et al. |
| 6,623,518 B2 | 9/2003 | Thompson et al. |
| 6,635,068 B1 | 10/2003 | Dubrul et al. |
| 6,635,079 B2 | 10/2003 | Unsworth et al. |
| 6,652,571 B1 | 11/2003 | White et al. |
| 6,656,206 B2 | 12/2003 | Corcoran et al. |
| 6,663,588 B2 | 12/2003 | DuBois et al. |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,676,668 B2 | 1/2004 | Mercereau et al. |
| 6,676,692 B2 | 1/2004 | Rabkin et al. |
| 6,676,698 B2 | 1/2004 | McGuckin, Jr. et al. |
| 6,682,558 B2 | 1/2004 | Tu et al. |
| 6,682,559 B2 | 1/2004 | Myers et al. |
| 6,689,144 B2 | 2/2004 | Gerberding |
| 6,689,164 B1 | 2/2004 | Seguin |
| 6,692,512 B2 | 2/2004 | Jang |
| 6,695,864 B2 | 2/2004 | Macoviak et al. |
| 6,695,865 B2 | 2/2004 | Boyle et al. |
| 6,702,851 B1 | 3/2004 | Chinn et al. |
| 6,712,836 B1 | 3/2004 | Berg |
| 6,712,842 B1 | 3/2004 | Gifford, III et al. |
| 6,712,843 B2 | 3/2004 | Elliott |
| 6,714,842 B1 | 3/2004 | Ito |
| 6,723,122 B2 | 4/2004 | Yang et al. |
| 6,730,118 B2 | 5/2004 | Spenser et al. |
| 6,730,377 B2 | 5/2004 | Wang |
| 6,733,525 B2 | 5/2004 | Yang et al. |
| 6,752,828 B2 | 6/2004 | Thornton |
| 6,758,855 B2 | 7/2004 | Fulton, III et al. |
| 6,764,503 B1 | 7/2004 | Ishimaru |
| 6,764,509 B2 | 7/2004 | Chinn et al. |
| 6,767,345 B2 | 7/2004 | St. Germain et al. |
| 6,773,454 B2 | 8/2004 | Wholey et al. |
| 6,776,791 B1 | 8/2004 | Stallings et al. |
| 6,790,218 B2 | 9/2004 | Jayaraman |
| 6,790,229 B1 | 9/2004 | Berreklouw |
| 6,790,230 B2 | 9/2004 | Beyersdorf et al. |
| 6,790,237 B2 | 9/2004 | Stinson |
| 6,792,979 B2 | 9/2004 | Konya et al. |
| 6,814,746 B2 | 11/2004 | Thompson et al. |
| 6,821,297 B2 | 11/2004 | Snyders |
| 6,837,901 B2 | 1/2005 | Rabkin et al. |
| 6,843,802 B1 | 1/2005 | Villalobos et al. |
| 6,849,085 B2 | 2/2005 | Marton |
| 6,863,668 B2 | 3/2005 | Gillespie et al. |
| 6,872,223 B2 | 3/2005 | Roberts et al. |
| 6,872,226 B2 | 3/2005 | Cali et al. |
| 6,875,231 B2 | 4/2005 | Anduiza et al. |
| 6,881,220 B2 | 4/2005 | Edwin et al. |
| 6,887,266 B2 | 5/2005 | Williams et al. |
| 6,890,340 B2 | 5/2005 | Duane |
| 6,893,459 B1 | 5/2005 | Macoviak |
| 6,893,460 B2 | 5/2005 | Spenser et al. |
| 6,905,743 B1 | 6/2005 | Chen et al. |
| 6,908,481 B2 | 6/2005 | Cribier |
| 6,911,036 B2 | 6/2005 | Douk et al. |
| 6,911,037 B2 | 6/2005 | Gainor |
| 6,913,614 B2 | 7/2005 | Marino et al. |
| 6,921,397 B2 | 7/2005 | Corcoran et al. |
| 6,936,058 B2 | 8/2005 | Forde et al. |
| 6,936,067 B2 | 8/2005 | Buchanan |
| 6,945,997 B2 | 9/2005 | Huynh |
| 6,951,571 B1 | 10/2005 | Srivastava |
| 6,953,332 B1 | 10/2005 | Kurk et al. |
| 6,960,220 B2 | 11/2005 | Marino et al. |
| 6,960,224 B2 | 11/2005 | Marino et al. |
| 6,974,464 B2 | 12/2005 | Quijano et al. |
| 6,974,476 B2 | 12/2005 | McGuckin, Jr. et al. |
| 6,979,350 B2 | 12/2005 | Moll et al. |
| 6,984,242 B2 | 1/2006 | Campbell et al. |
| 7,011,681 B2 | 3/2006 | Vesely |
| 7,018,406 B2 | 3/2006 | Seguin et al. |
| 7,025,791 B2 | 4/2006 | Evine et al. |
| 7,037,331 B2 | 5/2006 | Mitelberg et al. |
| 7,077,861 B2 | 7/2006 | Spence |
| 7,087,072 B2 | 8/2006 | Marino et al. |
| 7,115,135 B2 | 10/2006 | Corcoran et al. |
| 7,122,020 B2 | 10/2006 | Mogul |
| 7,144,410 B2 | 12/2006 | Marino et al. |
| 7,166,097 B2 | 1/2007 | Barbut |
| 7,175,653 B2 | 2/2007 | Gaber |
| 7,175,654 B2 | 2/2007 | Bonsignore et al. |
| 7,189,258 B2 | 3/2007 | Johnson et al. |
| 7,191,018 B2 | 3/2007 | Gielen et al. |
| 7,192,435 B2 | 3/2007 | Corcoran et al. |
| 7,201,772 B2 | 4/2007 | Schwammenthal et al. |
| 7,235,093 B2 | 6/2007 | Gregorich |
| 7,261,732 B2 | 8/2007 | Justino |
| 7,320,704 B2 | 1/2008 | Lashinski et al. |
| 7,329,279 B2 | 2/2008 | Haug et al. |
| 7,374,560 B2 | 5/2008 | Ressemann et al. |
| 7,381,219 B2 | 6/2008 | Salahieh et al. |
| 7,402,171 B2 | 7/2008 | Osborne |
| 7,413,563 B2 | 8/2008 | Corcoran et al. |
| 7,445,631 B2 | 11/2008 | Salahieh et al. |
| 7,455,689 B2 | 11/2008 | Johnson |
| 7,566,336 B2 | 7/2009 | Corcoran et al. |

(56) References Cited

U.S. PATENT DOCUMENTS

| | | |
|---|---|---|
| 7,582,104 B2 | 9/2009 | Corcoran et al. |
| 7,591,848 B2 | 9/2009 | Allen |
| 7,625,364 B2 | 12/2009 | Corcoran et al. |
| 7,632,298 B2 | 12/2009 | Hijlkema et al. |
| 7,658,748 B2 | 2/2010 | Marino et al. |
| 7,691,115 B2 | 4/2010 | Corcoran et al. |
| 7,712,606 B2 | 5/2010 | Salahieh et al. |
| 7,722,666 B2 | 5/2010 | Lafontaine |
| 7,748,389 B2 | 7/2010 | Salahieh et al. |
| 7,749,238 B2 | 7/2010 | Corcoran et al. |
| 7,780,725 B2 | 8/2010 | Haug et al. |
| 7,803,184 B2 | 9/2010 | McGuckin, Jr. et al. |
| 7,803,186 B1 | 9/2010 | Li |
| 7,824,442 B2 | 11/2010 | Salahieh et al. |
| 7,824,443 B2 | 11/2010 | Salahieh et al. |
| 7,896,915 B2 | 3/2011 | Guyenot |
| 7,905,901 B2 | 3/2011 | Corcoran et al. |
| 7,927,351 B2 | 4/2011 | Corcoran et al. |
| 7,972,361 B2 | 7/2011 | Corcoran et al. |
| 8,043,368 B2 | 10/2011 | Crabtree |
| 8,057,540 B2 | 11/2011 | Letac |
| 8,092,520 B2 | 1/2012 | Quadri |
| 8,167,935 B2 | 5/2012 | McGuckin, Jr. et al. |
| 8,236,049 B2 | 8/2012 | Rowe |
| 8,317,858 B2 | 11/2012 | Straubinger |
| 8,366,741 B2 | 2/2013 | Chin et al. |
| 8,398,708 B2 | 3/2013 | Meiri |
| 8,425,593 B2 | 4/2013 | Braido |
| 8,444,689 B2 | 5/2013 | Zhang |
| 8,449,599 B2 | 5/2013 | Chau et al. |
| 8,551,132 B2 | 10/2013 | Eskridge |
| 8,551,161 B2 | 10/2013 | Dolan |
| 8,562,672 B2 | 10/2013 | Bonhoeffer |
| 8,568,475 B2 | 10/2013 | Nguyen |
| 8,579,964 B2 | 11/2013 | Lane et al. |
| 8,579,966 B2 | 11/2013 | Seguin |
| 8,623,074 B2 | 1/2014 | Ryan |
| 8,628,566 B2 | 1/2014 | Eberhardt |
| 8,673,000 B2 | 3/2014 | Tabor |
| 8,685,080 B2 | 4/2014 | White |
| 8,721,708 B2 | 5/2014 | Sèguin |
| 8,728,155 B2 | 5/2014 | Montorfano et al. |
| 8,740,962 B2 | 6/2014 | Finch |
| 8,795,356 B2 | 8/2014 | Quadri |
| 8,801,779 B2 | 8/2014 | Seguin |
| 8,845,722 B2 | 9/2014 | Gabbay |
| 8,852,272 B2 | 10/2014 | Gross |
| 8,870,948 B1 | 10/2014 | Erzberger et al. |
| 8,894,702 B2 * | 11/2014 | Quadri .................. A61F 2/2409 623/1.36 |
| 8,911,455 B2 | 12/2014 | Quadri |
| 8,956,404 B2 | 2/2015 | Börtlein |
| 8,998,976 B2 | 4/2015 | Gregg |
| 9,011,527 B2 | 4/2015 | Li |
| 9,017,399 B2 | 4/2015 | Gross |
| 9,023,074 B2 | 5/2015 | Theobald |
| 9,023,100 B2 | 5/2015 | Quadri |
| 9,034,032 B2 | 5/2015 | McLean |
| 9,039,757 B2 | 5/2015 | McLean |
| 9,060,857 B2 | 6/2015 | Nguyen |
| 9,125,740 B2 | 9/2015 | Morriss |
| 9,132,009 B2 | 9/2015 | Hacohen |
| 9,155,617 B2 | 10/2015 | Carpentier |
| 9,168,130 B2 | 10/2015 | Straubinger |
| 9,168,131 B2 | 10/2015 | Yohanan |
| 9,186,249 B2 * | 11/2015 | Rolando ............... A61F 2/2418 |
| 9,289,291 B2 * | 3/2016 | Gorman, III ............ A61F 2/24 |
| 9,295,552 B2 * | 3/2016 | McLean ................ A61F 2/2409 |
| 9,387,071 B2 | 7/2016 | Tuval |
| 9,393,110 B2 | 7/2016 | Levi |
| 9,393,112 B2 | 7/2016 | Tuval |
| 9,414,852 B2 | 8/2016 | Gifford, III |
| 9,421,083 B2 | 8/2016 | Eidenschink |
| 9,421,098 B2 | 8/2016 | Gifford, III |
| 9,474,609 B2 | 10/2016 | Haverkost |
| 9,480,556 B2 | 11/2016 | Revuelta |
| 9,480,558 B2 | 11/2016 | Destefano |
| 9,498,330 B2 | 11/2016 | Solem |
| 9,504,564 B2 | 11/2016 | Nguyen |
| 9,504,568 B2 | 11/2016 | Ryan |
| 9,510,943 B2 | 12/2016 | Mesana |
| 9,532,870 B2 | 1/2017 | Cooper et al. |
| 9,572,662 B2 * | 2/2017 | Morriss ................ A61F 2/2445 |
| 9,579,198 B2 | 2/2017 | Deem |
| 9,655,722 B2 | 5/2017 | Morriss |
| 9,763,780 B2 * | 9/2017 | Morriss ................ A61F 2/2418 |
| 9,808,230 B2 | 11/2017 | Brown et al. |
| 9,883,941 B2 | 2/2018 | Hastings |
| 9,949,824 B2 | 4/2018 | Bonhoeffer |
| 10,004,601 B2 | 6/2018 | Tuval |
| 10,045,765 B2 | 8/2018 | Rafiee et al. |
| 10,052,201 B2 * | 8/2018 | Zhang ................... A61F 2/2418 |
| 10,117,744 B2 * | 11/2018 | Ratz ..................... A61F 2/2418 |
| 10,166,014 B2 * | 1/2019 | Thambar ............... A61F 2/2436 |
| 10,314,695 B2 | 6/2019 | Salahieh et al. |
| 10,441,412 B2 * | 10/2019 | Quadri .................. A61F 2/2436 |
| 10,702,380 B2 * | 7/2020 | Morriss ................ A61F 2/2436 |
| 10,842,621 B2 * | 11/2020 | Yu ....................... A61F 2/2409 |
| 11,154,396 B2 * | 10/2021 | Dibie ................... A61F 2/2418 |
| 11,324,594 B2 * | 5/2022 | Ratz ..................... A61F 2/2436 |
| 2001/0007956 A1 | 7/2001 | Letac et al. |
| 2001/0039450 A1 | 11/2001 | Pavcnik et al. |
| 2001/0041928 A1 | 11/2001 | Pavcnik et al. |
| 2001/0041930 A1 | 11/2001 | Globerman et al. |
| 2001/0044652 A1 | 11/2001 | Moore |
| 2001/0044656 A1 | 11/2001 | Williamson et al. |
| 2002/0002396 A1 | 1/2002 | Fulkerson |
| 2002/0010489 A1 | 1/2002 | Grayzel et al. |
| 2002/0026233 A1 | 2/2002 | Shaknovich |
| 2002/0029981 A1 | 3/2002 | Nigam |
| 2002/0032481 A1 | 3/2002 | Gabbay |
| 2002/0055769 A1 | 5/2002 | Wang |
| 2002/0062135 A1 | 5/2002 | Mazzocchi |
| 2002/0082609 A1 | 6/2002 | Green |
| 2002/0095173 A1 | 7/2002 | Mazzocchi et al. |
| 2002/0120328 A1 | 8/2002 | Pathak et al. |
| 2002/0161392 A1 | 10/2002 | Dubrul |
| 2002/0161394 A1 | 10/2002 | Macoviak et al. |
| 2002/0177766 A1 | 11/2002 | Mogul |
| 2002/0183781 A1 | 12/2002 | Casey et al. |
| 2002/0188341 A1 | 12/2002 | Elliott |
| 2002/0188344 A1 | 12/2002 | Bolea et al. |
| 2003/0023303 A1 | 1/2003 | Palmaz et al. |
| 2003/0036791 A1 | 2/2003 | Philipp et al. |
| 2003/0040771 A1 | 2/2003 | Hyodoh et al. |
| 2003/0040772 A1 | 2/2003 | Hyodoh et al. |
| 2003/0040791 A1 | 2/2003 | Oktay |
| 2003/0050694 A1 | 3/2003 | Yang et al. |
| 2003/0055495 A1 | 3/2003 | Pease et al. |
| 2003/0060844 A1 | 3/2003 | Borillo et al. |
| 2003/0070944 A1 | 4/2003 | Nigam |
| 2003/0074011 A1 | 4/2003 | Gilboa |
| 2003/0109924 A1 | 6/2003 | Cribier |
| 2003/0109930 A1 | 6/2003 | Bluni et al. |
| 2003/0114912 A1 | 6/2003 | Sequin et al. |
| 2003/0130729 A1 | 7/2003 | Paniagua et al. |
| 2003/0135257 A1 | 7/2003 | Taheri |
| 2003/0144732 A1 | 7/2003 | Cosgrove et al. |
| 2003/0149476 A1 | 8/2003 | Damm et al. |
| 2003/0149477 A1 | 8/2003 | Gabbay |
| 2003/0149478 A1 | 8/2003 | Figulla et al. |
| 2003/0176884 A1 | 9/2003 | Berrada et al. |
| 2003/0181850 A1 | 9/2003 | Diamond et al. |
| 2003/0187495 A1 | 10/2003 | Cully et al. |
| 2003/0199971 A1 | 10/2003 | Tower et al. |
| 2003/0208224 A1 | 11/2003 | Broome |
| 2003/0212429 A1 | 11/2003 | Keegan et al. |
| 2003/0212454 A1 | 11/2003 | Scott et al. |
| 2003/0216774 A1 | 11/2003 | Larson |
| 2003/0225421 A1 | 12/2003 | Peavey |
| 2003/0225445 A1 | 12/2003 | Derus et al. |
| 2003/0229390 A1 | 12/2003 | Ashton et al. |
| 2003/0233117 A1 | 12/2003 | Adams et al. |
| 2004/0034411 A1 | 2/2004 | Quijano et al. |

(56) References Cited

U.S. PATENT DOCUMENTS

| | | |
|---|---|---|
| 2004/0049224 A1 | 3/2004 | Buehlmann et al. |
| 2004/0049226 A1 | 3/2004 | Keegan et al. |
| 2004/0049262 A1 | 3/2004 | Obermiller et al. |
| 2004/0060563 A1 | 4/2004 | Rapacki |
| 2004/0082904 A1 | 4/2004 | Houde et al. |
| 2004/0082967 A1 | 4/2004 | Broome et al. |
| 2004/0087982 A1 | 5/2004 | Eskuri |
| 2004/0093016 A1 | 5/2004 | Root et al. |
| 2004/0093060 A1 | 5/2004 | Seguin |
| 2004/0098022 A1 | 5/2004 | Barone |
| 2004/0098098 A1 | 5/2004 | McGuckin et al. |
| 2004/0098099 A1 | 5/2004 | McCullagh et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0122468 A1 | 6/2004 | Yodfat et al. |
| 2004/0127849 A1 | 7/2004 | Kantor |
| 2004/0127936 A1 | 7/2004 | Salahieh et al. |
| 2004/0127979 A1 | 7/2004 | Wilson et al. |
| 2004/0133232 A1 | 7/2004 | Rosenbluth |
| 2004/0133274 A1 | 7/2004 | Webler et al. |
| 2004/0138694 A1 | 7/2004 | Tran et al. |
| 2004/0143294 A1 | 7/2004 | Corcoran et al. |
| 2004/0148021 A1 | 7/2004 | Cartledge et al. |
| 2004/0153094 A1 | 8/2004 | Dunfee et al. |
| 2004/0158277 A1 | 8/2004 | Lowe et al. |
| 2004/0167565 A1 | 8/2004 | Beulke et al. |
| 2004/0181140 A1 | 9/2004 | Falwell et al. |
| 2004/0186563 A1 | 9/2004 | Lobbi |
| 2004/0204755 A1 | 10/2004 | Robin |
| 2004/0215331 A1 | 10/2004 | Chew et al. |
| 2004/0215339 A1 | 10/2004 | Drasler et al. |
| 2004/0220655 A1 | 11/2004 | Swanson et al. |
| 2004/0225321 A1 | 11/2004 | Krolik et al. |
| 2004/0225354 A1 | 11/2004 | Allen |
| 2004/0236411 A1 | 11/2004 | Sarac et al. |
| 2004/0254636 A1 | 12/2004 | Flagle et al. |
| 2005/0033402 A1 | 2/2005 | Cully et al. |
| 2005/0038383 A1 | 2/2005 | Kelley |
| 2005/0070934 A1 | 3/2005 | Tanaka |
| 2005/0075662 A1 | 4/2005 | Pedersen et al. |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0090846 A1 | 4/2005 | Pedersen et al. |
| 2005/0096692 A1 | 5/2005 | Linder et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0100580 A1 | 5/2005 | Osborne et al. |
| 2005/0107822 A1 | 5/2005 | WasDyke |
| 2005/0113910 A1 | 5/2005 | Paniagua et al. |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137691 A1 | 6/2005 | Salahieh et al. |
| 2005/0137692 A1 | 6/2005 | Haug et al. |
| 2005/0137694 A1 | 6/2005 | Haug et al. |
| 2005/0137696 A1 | 6/2005 | Salahieh et al. |
| 2005/0137697 A1 | 6/2005 | Salahieh et al. |
| 2005/0137701 A1 | 6/2005 | Salahieh et al. |
| 2005/0143809 A1 | 6/2005 | Salahieh et al. |
| 2005/0165352 A1 | 7/2005 | Henry et al. |
| 2005/0182486 A1 | 8/2005 | Gabbay |
| 2005/0197694 A1 | 9/2005 | Pai et al. |
| 2005/0197695 A1 | 9/2005 | Stacchino et al. |
| 2005/0203614 A1 | 9/2005 | Forster et al. |
| 2005/0203615 A1 | 9/2005 | Forster et al. |
| 2005/0203616 A1 | 9/2005 | Cribier |
| 2005/0203617 A1 | 9/2005 | Forster et al. |
| 2005/0209580 A1 | 9/2005 | Freyman |
| 2005/0228472 A1 | 10/2005 | Case et al. |
| 2005/0251250 A1 | 11/2005 | Verhoeven et al. |
| 2005/0251251 A1 | 11/2005 | Cribier |
| 2005/0261759 A1 | 11/2005 | Lambrecht et al. |
| 2005/0267560 A1 | 12/2005 | Bates |
| 2005/0283962 A1 | 12/2005 | Boudjemline |
| 2005/0288766 A1 | 12/2005 | Plain |
| 2006/0004439 A1 | 1/2006 | Spenser et al. |
| 2006/0004442 A1 | 1/2006 | Spenser et al. |
| 2006/0015168 A1 | 1/2006 | Gunderson |
| 2006/0058872 A1* | 3/2006 | Salahieh ............ A61F 2/2439 623/2.18 |
| 2006/0116717 A1 | 6/2006 | Marino et al. |
| 2006/0149360 A1 | 7/2006 | Schwammenthal et al. |
| 2006/0155312 A1 | 7/2006 | Levine et al. |
| 2006/0161249 A1 | 7/2006 | Realyvasquez et al. |
| 2006/0190030 A1 | 8/2006 | To |
| 2006/0195183 A1 | 8/2006 | Navia et al. |
| 2006/0235510 A1 | 10/2006 | Johnson |
| 2006/0247680 A1 | 11/2006 | Amplatz |
| 2006/0253191 A1 | 11/2006 | Salahieh et al. |
| 2006/0259134 A1 | 11/2006 | Schwammenthal et al. |
| 2006/0259135 A1* | 11/2006 | Navia ............... A61F 2/2457 623/2.11 |
| 2006/0259137 A1 | 11/2006 | Artof |
| 2006/0265045 A1 | 11/2006 | Shiu |
| 2006/0271166 A1 | 11/2006 | Thill et al. |
| 2006/0287668 A1 | 12/2006 | Fawzi et al. |
| 2007/0016286 A1 | 1/2007 | Herrmann et al. |
| 2007/0055340 A1 | 3/2007 | Pryor |
| 2007/0088431 A1 | 4/2007 | Bourang |
| 2007/0100440 A1 | 5/2007 | Figulla |
| 2007/0112355 A1 | 5/2007 | Salahieh et al. |
| 2007/0118214 A1 | 5/2007 | Salahieh et al. |
| 2007/0203503 A1 | 8/2007 | Salahieh et al. |
| 2007/0203575 A1 | 8/2007 | Forster |
| 2007/0244552 A1 | 10/2007 | Salahieh et al. |
| 2007/0255389 A1 | 11/2007 | Oberti |
| 2007/0265656 A1 | 11/2007 | Amplatz |
| 2007/0276324 A1 | 11/2007 | Laduca et al. |
| 2007/0288089 A1 | 12/2007 | Gurskis et al. |
| 2008/0015619 A1 | 1/2008 | Figulla |
| 2008/0033543 A1 | 2/2008 | Gurskis |
| 2008/0082165 A1 | 4/2008 | Wilson et al. |
| 2008/0140189 A1 | 6/2008 | Nguyen |
| 2008/0140191 A1 | 6/2008 | Mathis |
| 2008/0167682 A1 | 7/2008 | Corcoran et al. |
| 2008/0177381 A1 | 7/2008 | Navia |
| 2008/0188928 A1 | 8/2008 | Salahieh et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0234797 A1 | 9/2008 | Styrc |
| 2008/0288054 A1 | 11/2008 | Pulnev et al. |
| 2009/0005863 A1 | 1/2009 | Goetz et al. |
| 2009/0036768 A1 | 2/2009 | Seehusen |
| 2009/0062841 A1 | 3/2009 | Amplatz |
| 2009/0082803 A1 | 3/2009 | Adams |
| 2009/0112309 A1 | 4/2009 | Jaramillo et al. |
| 2009/0171456 A1 | 7/2009 | Kveen et al. |
| 2009/0182405 A1 | 7/2009 | Arnault De La Menardiere et al. |
| 2009/0192585 A1 | 7/2009 | Bloom et al. |
| 2009/0222076 A1* | 9/2009 | Figulla ............... A61F 2/2436 623/1.2 |
| 2009/0254165 A1 | 10/2009 | Tabor et al. |
| 2009/0264759 A1 | 10/2009 | Byrd |
| 2009/0287290 A1 | 11/2009 | Macaulay et al. |
| 2009/0306768 A1 | 12/2009 | Quadri |
| 2010/0036479 A1* | 2/2010 | Hill ............... A61F 2/2418 623/1.26 |
| 2010/0049313 A1 | 2/2010 | Alon et al. |
| 2010/0094314 A1 | 4/2010 | Hernlund |
| 2010/0114308 A1 | 5/2010 | Maschke |
| 2010/0121434 A1 | 5/2010 | Paul et al. |
| 2010/0161036 A1 | 6/2010 | Pintor |
| 2010/0219092 A1 | 9/2010 | Salahieh et al. |
| 2010/0234878 A1 | 9/2010 | Hruska et al. |
| 2010/0268204 A1 | 10/2010 | Tieu |
| 2010/0280495 A1 | 11/2010 | Paul et al. |
| 2010/0284724 A1 | 11/2010 | Cardia |

(56) References Cited

U.S. PATENT DOCUMENTS

| | | |
|---|---|---|
| 2010/0298931 A1 | 11/2010 | Quadri |
| 2010/0312333 A1 | 12/2010 | Navia et al. |
| 2011/0004296 A1 | 1/2011 | Lutter |
| 2011/0022157 A1 | 1/2011 | Essinger |
| 2011/0029072 A1 | 2/2011 | Gabbay |
| 2011/0034987 A1 | 2/2011 | Kennedy |
| 2011/0166636 A1 | 7/2011 | Rowe |
| 2011/0218619 A1 | 9/2011 | Benichou |
| 2011/0245911 A1 | 10/2011 | Quill |
| 2011/0257723 A1 | 10/2011 | McNamara |
| 2011/0264196 A1 | 10/2011 | Savage et al. |
| 2011/0264198 A1 | 10/2011 | Murray, III |
| 2011/0295363 A1 | 12/2011 | Girard |
| 2011/0301702 A1 | 12/2011 | Rust |
| 2011/0319989 A1* | 12/2011 | Lane .................... A61F 2/2418 623/2.11 |
| 2012/0016464 A1 | 1/2012 | Seguin |
| 2012/0022640 A1* | 1/2012 | Gross .................... A61F 2/2439 623/2.11 |
| 2012/0059458 A1 | 3/2012 | Buchbinder |
| 2012/0078360 A1 | 3/2012 | Rafiee |
| 2012/0101572 A1 | 4/2012 | Kovalsky |
| 2012/0158629 A1 | 6/2012 | Duffy |
| 2012/0197391 A1 | 8/2012 | Alkhatib |
| 2012/0303116 A1* | 11/2012 | Gorman, III .......... A61F 2/2436 623/2.11 |
| 2012/0323316 A1* | 12/2012 | Chau .................... A61F 2/246 623/2.37 |
| 2013/0018449 A1 | 1/2013 | Bailey et al. |
| 2013/0041447 A1 | 2/2013 | Erb et al. |
| 2013/0041458 A1 | 2/2013 | Lashinski et al. |
| 2013/0304197 A1 | 11/2013 | Buchbinder |
| 2013/0310923 A1 | 11/2013 | Arash |
| 2013/0310928 A1* | 11/2013 | Morriss ................ A61F 2/2409 623/2.18 |
| 2014/0005778 A1* | 1/2014 | Buchbinder .......... A61F 2/2445 623/2.37 |
| 2014/0012368 A1 | 1/2014 | Sugimoto |
| 2014/0012374 A1 | 1/2014 | Rankin |
| 2014/0052237 A1* | 2/2014 | Lane .................... A61F 2/2436 623/2.11 |
| 2014/0052241 A1 | 2/2014 | Harks |
| 2014/0052244 A1 | 2/2014 | Rolando |
| 2014/0081383 A1 | 3/2014 | Eberhardt |
| 2014/0107665 A1 | 4/2014 | Shellenberger |
| 2014/0180391 A1 | 6/2014 | Dagan |
| 2014/0214157 A1 | 7/2014 | Bortlein et al. |
| 2014/0214159 A1 | 7/2014 | Robert |
| 2014/0249622 A1* | 9/2014 | Carmi .................... A61F 2/2418 623/2.11 |
| 2014/0324164 A1 | 10/2014 | Gross |
| 2014/0358222 A1* | 12/2014 | Gorman, III .......... A61F 2/2418 623/2.11 |
| 2015/0094802 A1 | 4/2015 | Buchbinder |
| 2015/0142100 A1 | 5/2015 | Morriss |
| 2015/0157457 A1 | 6/2015 | Hacohen |
| 2015/0173897 A1* | 6/2015 | Raanani ................ A61F 2/2436 623/2.11 |
| 2015/0196390 A1* | 7/2015 | Ma ........................ A61F 2/2412 623/2.17 |
| 2015/0216661 A1* | 8/2015 | Hacohen ................ A61F 2/2409 623/2.37 |
| 2015/0272737 A1* | 10/2015 | Dale .................... A61F 2/2418 623/2.37 |
| 2015/0305860 A1* | 10/2015 | Wang .................... A61L 27/507 623/2.38 |
| 2015/0328002 A1* | 11/2015 | McLean ................ A61F 2/2412 623/2.36 |
| 2015/0351903 A1* | 12/2015 | Morriss ................ A61F 2/2418 623/2.11 |
| 2016/0030169 A1 | 2/2016 | Shahriari |
| 2016/0038280 A1 | 2/2016 | Morriss |
| 2016/0051362 A1 | 2/2016 | Cooper et al. |
| 2016/0158003 A1 | 6/2016 | Wallace |
| 2016/0166384 A1 | 6/2016 | Olson |
| 2016/0310267 A1 | 10/2016 | Zeng et al. |
| 2017/0035569 A1 | 2/2017 | Deem |
| 2017/0056169 A1 | 3/2017 | Johnson et al. |
| 2017/0095328 A1* | 4/2017 | Cooper .................. A61F 2/2418 |
| 2017/0100236 A1* | 4/2017 | Robertson ............. A61F 2/2403 |
| 2017/0128199 A1* | 5/2017 | Gurovich .............. A61F 2/2418 |
| 2017/0209261 A1 | 7/2017 | Börtlein |
| 2017/0209269 A1 | 7/2017 | Conklin |
| 2017/0231762 A1 | 8/2017 | Quadri |
| 2017/0245991 A1 | 8/2017 | Granada |
| 2017/0354497 A1* | 12/2017 | Quadri .................. A61F 2/2415 |
| 2018/0021133 A1 | 1/2018 | Barbarino |
| 2018/0110622 A1 | 4/2018 | Gregg |
| 2018/0296341 A1 | 10/2018 | Noe et al. |
| 2018/0325662 A1* | 11/2018 | Modine ................ A61F 2/2487 |
| 2020/0306044 A1* | 10/2020 | Ratz .................... A61F 2/2463 |
| 2021/0361418 A1* | 11/2021 | Li ........................ A61L 27/16 |

FOREIGN PATENT DOCUMENTS

| | | |
|---|---|---|
| EP | 0409929 | 1/1991 |
| EP | 0409929 B1 | 1/1991 |
| EP | 0819013 | 1/1998 |
| EP | 0819013 B1 | 1/1998 |
| EP | 0937439 | 8/1999 |
| EP | 0937439 B1 | 8/1999 |
| EP | 1042045 | 10/2000 |
| EP | 1042045 B1 | 10/2000 |
| EP | 1057459 A1 | 12/2000 |
| EP | 1057460 A1 | 12/2000 |
| EP | 1059894 | 12/2000 |
| EP | 1059894 B1 | 12/2000 |
| EP | 1078610 | 2/2001 |
| EP | 1078610 B1 | 2/2001 |
| EP | 1229864 | 8/2002 |
| EP | 1229864 B1 | 8/2002 |
| EP | 1340473 A2 | 9/2003 |
| EP | 1356793 A2 | 10/2003 |
| EP | 1430853 A2 | 6/2004 |
| EP | 1469797 | 10/2004 |
| EP | 1469797 B1 | 11/2005 |
| EP | 1600121 A1 | 11/2005 |
| EP | 1616531 A2 | 1/2006 |
| EP | 1819304 A2 | 8/2007 |
| EP | 1849440 A1 | 10/2007 |
| EP | 1849449 A1 | 10/2007 |
| EP | 2124826 | 12/2009 |
| EP | 2654624 A1 | 10/2013 |
| WO | 9504556 A2 | 2/1995 |
| WO | 9529640 A1 | 11/1995 |
| WO | 9614032 A1 | 5/1996 |
| WO | 9624306 A1 | 8/1996 |
| WO | 9836790 A1 | 8/1998 |
| WO | 9857599 A2 | 12/1998 |
| WO | 9944542 A2 | 9/1999 |
| WO | 0009059 A2 | 2/2000 |
| WO | 0044308 A2 | 8/2000 |
| WO | 200044313 A1 | 8/2000 |
| WO | 0067661 A2 | 11/2000 |
| WO | 0105331 A1 | 1/2001 |
| WO | 0135870 A1 | 5/2001 |
| WO | 0149213 | 7/2001 |
| WO | 0164137 A1 | 9/2001 |
| WO | 0236048 A1 | 5/2002 |
| WO | 2002041789 A2 | 5/2002 |
| WO | 02100297 A2 | 12/2002 |
| WO | 2003003943 A2 | 1/2003 |
| WO | 2003003949 A2 | 1/2003 |
| WO | 03011195 A2 | 2/2003 |
| WO | 03015851 A1 | 2/2003 |
| WO | 2003030776 A2 | 4/2003 |
| WO | 03094797 A1 | 11/2003 |
| WO | 2004014256 A1 | 2/2004 |
| WO | 2004019811 A2 | 3/2004 |
| WO | 2004026117 A2 | 4/2004 |
| WO | 2004041126 A1 | 5/2004 |
| WO | 2004047681 A1 | 6/2004 |

(56) References Cited

FOREIGN PATENT DOCUMENTS

| | | |
|---|---|---|
| WO | 2004066876 A1 | 8/2004 |
| WO | 2004082536 A1 | 9/2004 |
| WO | 2005037361 A2 | 4/2005 |
| WO | 2005084595 A1 | 9/2005 |
| WO | 2005087140 A1 | 9/2005 |
| WO | 2009072122 A1 | 6/2009 |
| WO | 2009108615 A1 | 9/2009 |
| WO | 2009132187 A1 | 10/2009 |
| WO | 2009137755 A2 | 11/2009 |
| WO | 2010057262 A1 | 5/2010 |
| WO | 2010141847 A1 | 12/2010 |
| WO | 2011057087 A1 | 5/2011 |
| WO | 2011081997 A1 | 7/2011 |
| WO | 2012161786 A1 | 11/2012 |

OTHER PUBLICATIONS

Atwood et al.; Insertion of Heart Valves by Catheterization; Project Supervised by Prof. S. Muftu of Northeastern University, May 2002: pp. 36-40.

Bodnar et al. Replacement Cardiac Valves R Chapter 13: Extinct cardiac valve prostheses. Pergamon Publishing Corporation. New York, 1991: 307-322 (year of pub. sufficiently earlier than effective US filing date and any foreign priority date).

Boudjemline et al. "Percutaneous implantation of a valve in the descending aorta in lambs." Euro. Heart J; Jul. 2002; 23: 1045-1049.

Boudjemline et al. "Percutaneous pulmonary valve replacement in a large right ventricular outflow tract: an experimental study." Journal of the American College of Cardiology; Mar. 2004; vol. 43(6): 1082-1087.

Boudjemline et al. "Percutaneous valve insertion: A new approach?" J. of Thoracic and Cardio. Surg; Mar. 2003; 125(3): 741-743.

Boudjemline et al. "Steps Toward Percutaneous Aortic Valve Replacement." Circulation; Feb. 2002; 105: 775-778.

Cribier et al. "Early Experience with Percutaneous Transcatheter Implantation of Heart Valve Prosthesis for the Treatment of End-Stage Inoperable Patients with Calcific Aortic Stenosis." J. of Am. Coll. of Cardio; Feb. 2004; 43(4): 698-703.

Cribier et al. "Percutaneous Transcatheter Implantation of an Aortic Valve Prosthesis for Calcific Aortic Stenosis: First Human Case." Percutaneous Valve Technologies, Inc. 2002: 16 pages (year of pub. sufficiently earlier than effective US filedand any foreign priority date).

Ferrari et al. "Percutaneous transvascular aortic valve replacement with self expanding stent-valve device." Poster from the presentation given at SMIT 2000, 12th International Conference. 1 pg. Sep. 5, 2000.

Hijazi "Transcatheter Valve Replacement: A New Era of Percutaneous Cardiac Intervention Begins." J. of Am. College of Cardia; Mar. 2004; 43(6): 1088-1089.

Huber et al. "Do valved stents compromise coronary flow?" European Journal of Cardio-thoracic Surgery; May 2004; vol. 25: 754-759.

Knudsen et al. "Catheter-implanted prosthetic heart valves." Int'l J. of Art. Organs; May 1993; 16(5): 253-262.

Kort et al. "Minimally invasive aortic valve replacement: Echocardiographic and clinical results." Am. Heart J; Sep. 2001; 142(3): 476-481.

Love et al. The Autogenous Tissue Heart Valve: Current Stat. Journal of Cardiac Surgery; Dec. 1991; 6(4): 499-507.

Lutter et al. "Percutaneous aortic valve replacement: An experimental study. I. Studies on implantation." J. of Thoracic and Cardio. Surg; Apr. 2002; 123(4 ): 768-776.

Moulopoulos et al. "Catheter-Mounted Aortic Valves." Annals of Thoracic Surg; May 1971; 11(5): 423-430.

Paniagua et al. "Percutaneous heart valve in the chronic in vitro testing model." Circulation; Sep. 2002; 106: e51-e52.

Paniagua et al. Heart Watch (2004). Texas Heart Institute. Spring Mar. 2004 Edition: 8 pages.

Pavcnik et al. "Percutaneous bioprosthetic veno valve: A long-term study in sheep." J. of Vascular Surg; Mar. 2002; 35(3): 598-603.

Phillips et al. "A Temporary Catheter-Tip Aortic Valve: Hemodynamic Effects on Experimental Acute Aortic Insufficiency." Annals of Thoracic Surg; Feb. 1976; 21 (2): 134-136.

Sochman et al. "Percutaneous Transcatheter Aortic Disc Valve Prosthesis Implantation: A Feasibility Study." Cardiovasc. Lntervent. Radiol; Sep.-Oct. 2000; 23: 384-388.

Stuart, M. "In Heart Valves, a Brave, New Non-Surgical World." Start-Up; Feb. 2004: 9-17.

Vahanian et al. "Percutaneous Approaches to Valvular Disease." Circulation; Apr. 2004; 109:1572-1579.

Zhou et al. "Self-expandable valved stent of large size: off-bypass implantation in pulmonary position." Eur. J. Cardiothorac; Aug. 2003; 24: 212-216.

Boudjemline et al. Percutaneous implantation of a biological valve in the aorta to treat aortic valve insufficiency—a sheep study.f Med Sci. Monit; Apr. 2002; vol. 8, No. 4: BR113-116.

Cribier et al. "Percutaneous Transcatheter Implantation of an Aortic Valve Prosthesis for Calcific Aortic Stenosis: First Human Case Description." Circulation; Dec. 2002; 106: 3006-3008.

Cribier et al. "Percutaneous Transcatheter Implantation of an Aortic Valve Prosthesis for Calcific Aortic Stenosis: First Human Case." (slide presentation); TCT 2002 (conference); 16 pgs.; Washington D.C.; Sep. 24-28, 2002.

Erzberger et al.; U.S. Appl. No. 14/170,388 entitled "System and method for cardiac valve repair and replacement," filed Jan. 31, 2014.

Granada et al.; U.S. Appl. No. 14/677,320 entitled "Replacement cardiac valves and methods of use and manufacture," filed Apr. 2, 2015.

Granada et al.; U.S. Appl. No. 14/677,334 entitled "Replacement cardiac valves and methods of use and manufacture, " filed Apr. 2, 2015.

Granada et al.; U.S. Appl. No. 14/677,370 entitled "Replacement cardiac valves and methods of use and manufacture, " filed Apr. 2, 2015.

Granada et al.; U.S. Appl. No. 14/677,398 entitled "System and method for cardiac valve repair and replacement," filed Apr. 2, 2015.

Granada et al.; U.S. Appl. No. 15/688,701 entitled "System and method for cardiac valve repair and replacement," filed Aug. 28, 2017.

Hijazi "Transcatheter Valve Replacement: A New Era of Percutaneous Cardiac Intervention Begins." J. of Am. College of Cardio; Mar. 2004; 43(6): 1088-1089.

Love et al. The Autogenous Tissue Heart Valve: Current Stat.f Journal of Cardiac Surgery; Dec. 1991; 6(4): 499-507.

Noe et al.; U.S. Appl. No. 15/908,701 entitled "Replacement mitral valves," filed Feb. 28, 2018.

Noe et al.; U.S. Appl. No. 15/909,881 entitled "Replacement mitral valves," filed Mar. 1, 2018.

Noe et al.; U.S. Appl. No. 15/910,484 entitled "Replacement mitral valves," filed Mar. 2, 2018.

Sochman et al. "Percutaneous Transcatheter Aortic Disc Valve Prosthesis Implantation: A Feasibility Study." Cardiovasc. Intervent. Radiol; Sep.-Oct. 2000; 23: 384-388.

Solvay; Novel revivent(tm) Myocardial anchoring system from bioVentrix uses solvay's zeniva® PEEK in tether component; 3 pages retrieved from the internet (http://www.solvay.com/en/media/press_release/20131205-novel-revivent-myocardial-anchoring-system-bioventrix-uses-zenivapeek.html); (Press Release); on Aug. 10, 2017.

Van Herwerden et al."Percutaneous valve implantation: back to the future?" Euro. Heart J; Sep. 2002; 23(18): 1415-1416.

Wallace et al.; U.S. Appl. No. 15/669,788 entitled "Replacement cardiac valves and methods of use and manufacture," filed Aug. 4, 2017.

Wallace et al.; U.S. Appl. No. 15/669,805 entitled "Replacement mitral valves;" filed Aug. 4, 2017.

(56) References Cited

OTHER PUBLICATIONS

Wallace et al.; U.S. Appl. No. 15/688,673 entitled "Replacement mitral valves," filed Aug. 28, 2017.

* cited by examiner

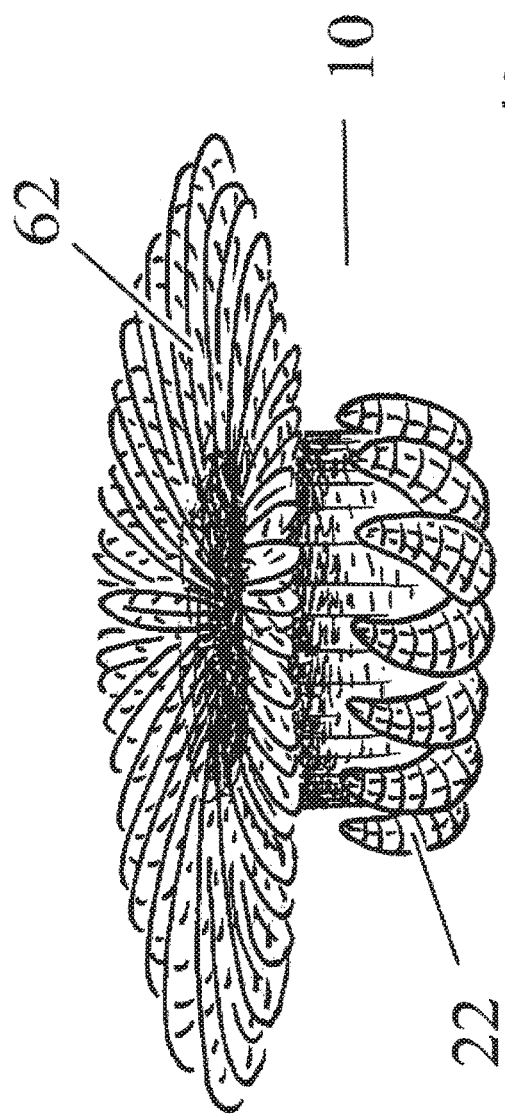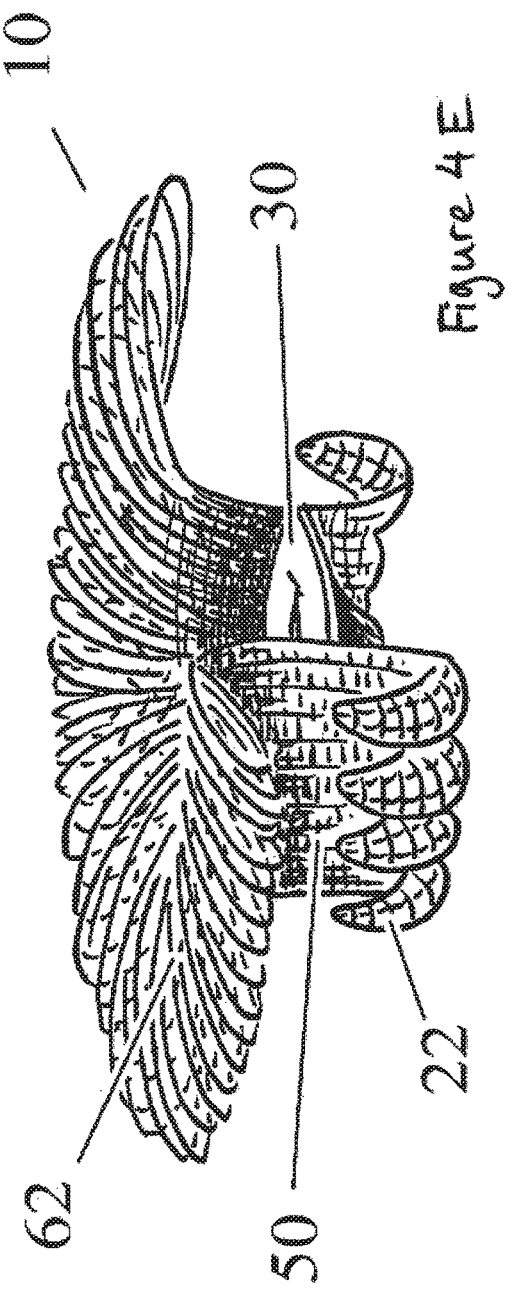

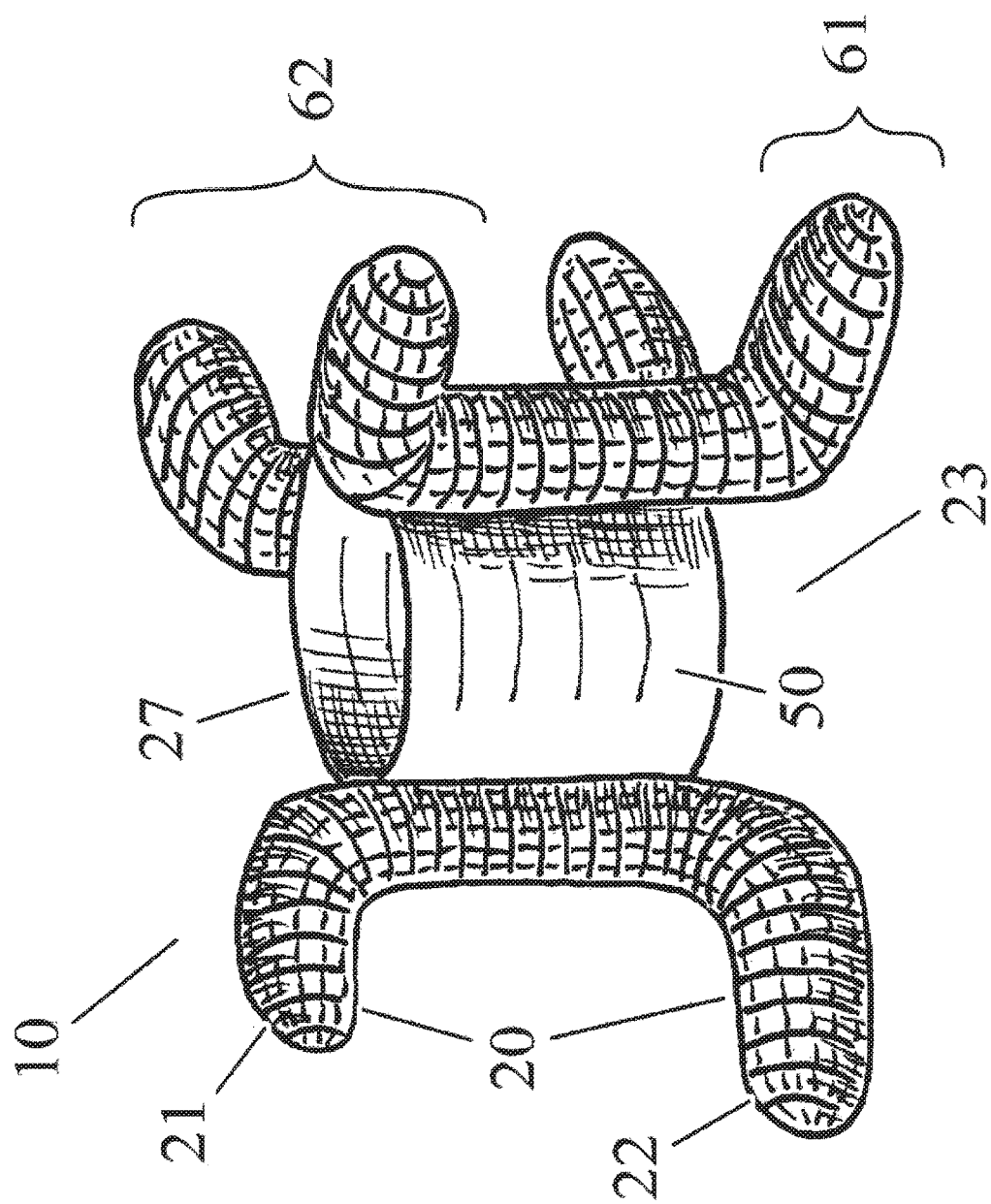

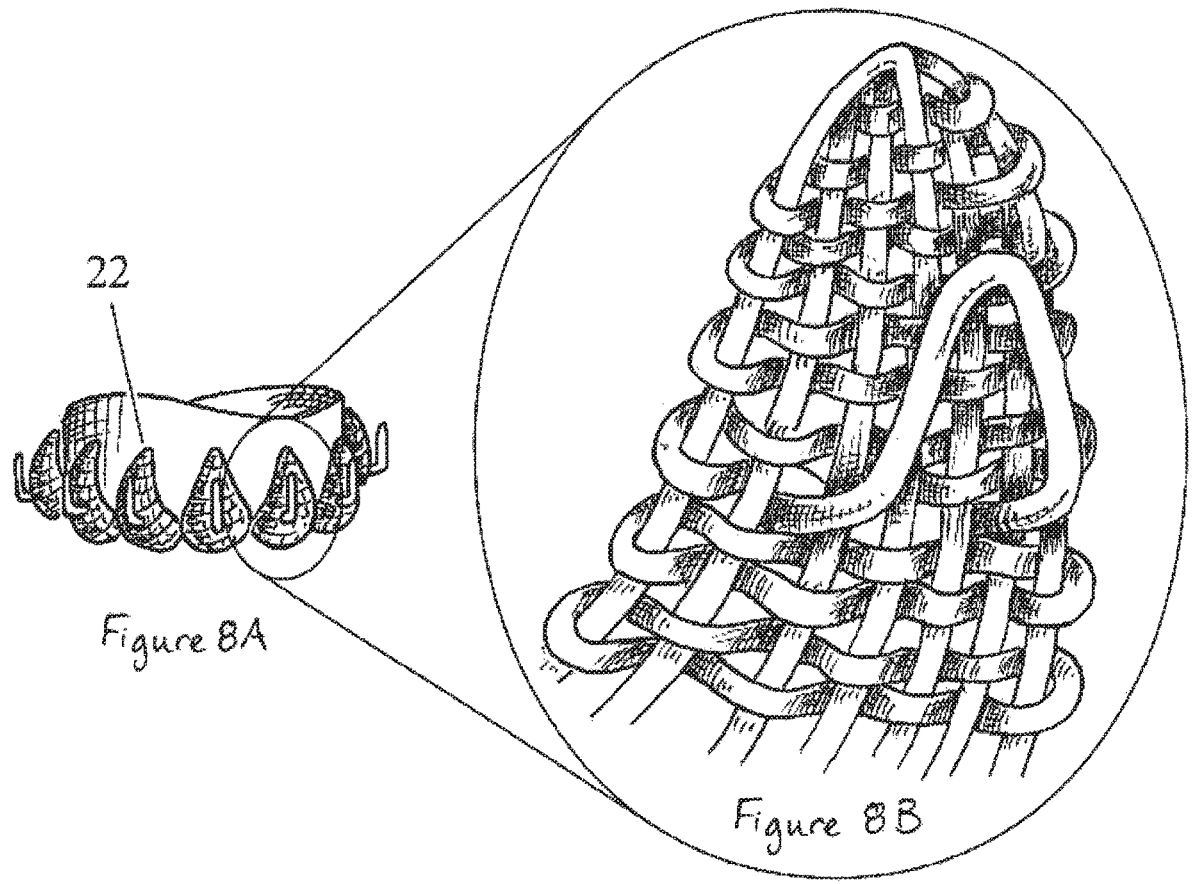
Figure 8A
Figure 8B
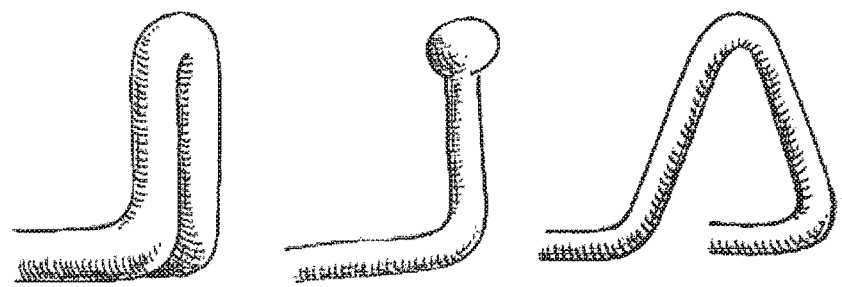
Figure 8C

DISK-BASED VALVE APPARATUS AND METHOD FOR THE TREATMENT OF VALVE DYSFUNCTION

CROSS-REFERENCE TO RELATED APPLICATIONS

This application is a continuation of U.S. patent application Ser. No. 14/281,714, filed May 19, 2014, which is a division of U.S. patent application Ser. No. 14/033,185, filed Sep. 20, 2013, now U.S. Pat. No. 8,728,155, which is a continuation of International Application No. PCT/IB2012/000563, filed Mar. 21, 2012, which application claims the benefit of priority of commonly assigned U.S. Patent Application No. 61/454,703, filed Mar. 21, 2011, and entitled "Multiple Disk Self-Positioning Apparatus and Method for the Treatment of Valve Dysfunction".

FIELD OF THE INVENTION

The present invention generally relates to valve implantation and more specifically to the percutaneous replacement of dysfunctional valves.

BACKGROUND OF THE INVENTION a) Transcatheter Aortic Valve Implantation (TA VI)

In addition to the initial commercially approved devices for transcatheter aortic valve implantation (TAVI) such as the Edwards-Sapien™ THV balloon expandable bovine bioprosthesis (Edwards Lifesciences INC, Irvine, California, USA) and the Core Valve ReValving® System (Medtronic Inc., Minneapolis, Minnesota, USA), nitinol porcine self-expanding bioprosthesis, a number of newer devices have also recently been CE marked for use via the transapical route. These are the Symetis Acurate (Symetis, Lausanne, Switzerland) and the Jena Valve (JenaValve, Munich, Germany) that are described below in the text.

Several valves for TAVI are currently at an early stage of pre-clinical or clinical evaluation. Referring to Table 1, in general, new valves incorporate features aiming to reduce delivery catheter diameter, facilitate accurate positioning, reduce para-valvular leaks, or allow device retrieval. In the following paragraphs we will describe some of the publicly known programs.

The Direct Flow Medical Aortic Valve, developed by Direct Flow Medical Inc., USA and shown by D in FIG. 1, is a stent-less, non-metallic, expandable device that consists of bovine pericardial leaflets sewed to a Dacron fabric cuff, with an inflatable ring on the aortic side and another on the ventricular side, designed for trans-femoral delivery. Once the valve is positioned, the rings are inflated with saline and contrast until the position and function of the valve has been confirmed. The diluted contrast is then exchanged for an active polymeric medium that, following polymerization, hardens and forms the final support structure.

The Lotus Valve System developed by Boston Scientific Inc., USA, as shown by FIG. 1, is a bioprosthesis consisting of three bovine pericardial leaflets suspended in a self-expanding and self-centering braided nitinol stent frame. It has an active shortening-locking mechanism and an external polyurethane sealing membrane to prevent para-valvular leaks. In the delivery catheter the stent it is in its longitudinal form, with low radial force and small profile. Once the valve has been positioned and the outer catheter is retracted, the prosthesis expands radially, gaining radial force and losing height, effectively locking the valve in place. The valve is designed for trans-femoral delivery.

The Heart Leaflet Technologies ("HLT") valve, developed by Heart Leaflet Technologies Inc., USA, and as shown by A in FIG. 1, is a porcine pericardial trileaflet valve mounted in a self-inverting nitinol cuff, with 3 nitinol support hoops and with an antireflux collar, designed for trans-femoral delivery.

The JenaClip, developed by Jena Valve Technology GmbH, Munich, Germany and shown by C in FIG. 1, is a bioprosthetic pericardial tissue valve mounted in a self-expanding nitinol stent, as known as the JenaClip, that is built up of 2 layers of "paper clip-like" structures (3 in each layer) that are compressed in a dedicated delivery catheter. It has been designed anatomically to fit in the sinuses of Valsalva with a clip-based anchoring system 20. It is designed for both trans-femoral and trans-apical delivery and recently had CE mark for the transapical route.

The Engager valve, formerly developed by Ventor, recently acquired by Medtronic, Minneapolis, Minnesota, and shown by H in FIG. 1, is a self-expandable pericardial-tissue prosthesis with a composite nitinol proprietary frame. The outer frame has a crown-shape, with troughs that flare out to anchor the valve in the sinuses. An inner frame has an hourglass shape and is designed to minimize pressure loss at inlet and maximize pressure recovery at outlet, and thereby optimizing fluid dynamics (based on the Venturi effect). This device is specifically dedicated for trans-apical delivery, but more recently a trans-femoral version has been developed.

The AorTx Device, developed by Hansen Medical Inc., Mountain View, California and shown by F in FIG. 1, is a suture-less prosthesis that consists of a pericardial-tissue valve attached to a self-expanding, solid nitinol frame. This frame is folded before deployment. It is repositionable and retrievable. This valve has been designed for both trans-apical and femoral approach through an 18F delivery system. The ATS 3*f* Series, developed by ATS Medical, Minneapolis, Minnesota and shown by E in FIG. 1, is a self-expandable bioprosthesis mounted in a tubular nitinol frame designed for surgical (ATS 3*f* Enable) and percutaneous (ATS 3*f* Entrata) deployments. Six sizes are available, from 19 to 29 mm. The Perceval-Percutaneous, developed by the Sorin Group, Milan, Italy and shown by G in FIG. 1 is a self-expandable bovine pericardial valve with a nitinol panel frame matching the anatomy of the aortic root and sinuses of Valsalva. It has a double sheath that provides enhanced sealing and non-expandable support rods.

The Bailey-Palmaz Perc Valve, developed by Advanced Bio Prosthesis Surfaces, Ltd. San Antonio, Texas (not shown) is a completely mechanical valve consisting of a monolithic structure of nanosythesized nitinol in a self-expanding cage and nitinol leaflets that also has a nitinol membrane at the base of the valve to reduce paravalvular regurgitation. This new nanosynthetic material has improved stress and fracture resistance and has allowed for a device with a smaller profile, which can be delivered through a 10F sheath. It is designed to be repositionable and retrievable, and to be delivered by retrograde, antegrade, or transapical approach.

The Paniagua Heart Valve, developed by Endoluminal Technology Research, Miami, Florida and shown by H in FIG. 1, is a biologic valve having a collapsed profile of 2 mm that must be manually crimped on to a delivery balloon, but that also exists as a self-expanding model. It can be inserted through a 10F to 18F sheath, depending on the mounting frame and the final valve diameter. This valve was designed to be used in any heart valve position.

Symetis Acurate valve (Symetis, Lausanne, Switzerland) is a self-expanding nitinol stent has also recently been CE marked for use via the transapical route. The valve is porcine with the stent allowing anchorage via an upper and lower crown along with 3 stabilization arches in a subcoronary position, believed to be the 'anatomically correct' position. It is available in 3 sizes: 23 mm, 25 mm and 27 mm, with the ability to be planted sheathless (28 Fr equivalent). The transfemoral version is currently undergoing pre-clinical studies.

Although these valves may incorporate desirable features, little information is currently available on their efficacy, procedural outcomes, and durability.

b) Percutaneous Transcatheter Mitral Valve Repair ("MVR")

Recently, new techniques have been developed to treat mitral regurgitation ("MR") with percutaneous approach, in order to restore valve function without surgical incision and cardio-pulmonary by-pass.

Recently a new classification of percutaneous MVR technologies on the basis of functional anatomy grouping the devices into those targeting the leaflets (percutaneous leaflet plication, percutaneous leaflet coaptation, percutaneous leaflet ablation), the annulus (indirect: coronary sinus approach or an asymmetrical approach; direct: true percutaneous or a hybrid approach), the chordae (percutaneous chordal implantation), or the LV (percutaneous LV remodeling) has been proposed, as shown in Table 2.

1. Devices Targeting the Leaflets:
   a) Leaflet Plication.

This technology is based on the surgical Alfieri technique which brings the anterior and posterior leaflets together with a suture, creating a "double orifice" MV. This re-establishes leaflet coaptation, thereby reducing MR.

As example, the MitraClip system, developed by Abbott Vascular, Santa Clara, California, uses a steerable catheter to deliver a clip to the anterior leaflet and posterior leaflet via trans-septal access. The EVEREST I, developed by Endovascular Valve Edge-to-Edge REpair Study, which was a safety and feasibility study assessing this device has been recently published. Data from the EVEREST II study, randomizing Mitra-Clip versus surgical repair, were recently presented. The device is currently CE marked and used in clinical practice in Europe.

Also, the MitraFlex, developed by TransCardiac Therapeutics, Atlanta, Georgia, which deploys a clip to the leaflets via the transapical route, is undergoing pre-clinical testing (this device also allows an artificial chord to be implanted during the same procedure).

b) Leaflet Ablation.

Radiofrequency energy is delivered to the leaflet(s) to effect structural (fibrosis) or functional (reduced motion) alteration.

As example, the Thermocool irrigation ablation electrode, developed by BiosenseWebster, Inc., Diamond Bar, California, is a radiofrequency ablation catheter delivered through femoral approach retrogradely into the LV. The catheter is placed in contact with the anterior leaflet, and radiofrequency is delivered, causing scarring and fibrosis and reduced leaflet motion. Proof of concept was demonstrated in an animal study.

c) Leaflet Space Occupier.

The device acting is positioned across the MV orifice to provide a surface against which the leaflets can coapt, reducing MR.

As example, the Percu-Pro device, developed by Cardiosolutions, Stoughton, Massachusetts, consists of a polyurethane-silicone polymer space-occupying buoy that is anchored at the apex through the MV acting as a "spacer" in the mitral orifice. A trans-septal approach is required to implant the anchor in the apex. A phase 1 trial is ongoing.

2. Devices Targeting the Annulus:
   a) Indirect Annuloplasty

This approach mimics surgical annuloplasty rings, which are commonly used for repair of both degenerative and functional MR.

Coronary Sinus ("CS") Approach: This approach involves implantation of devices within the CS with the aim of "pushing" the posterior annulus anteriorly, thereby reducing the septal-lateral (anterior-posterior) dimension of the MA.

As example, the Monarc (previously Viking) system developed by Edwards Lifesciences consists of an outer guide catheter, a smaller delivery catheter, and a nitinol implant. The implant has 3 sections: distal and proximal self-expanding anchors, and a springlike CS and distal great cardiac vein closer, indirectly displacing the posterior annulus anteriorly. The phase 1 trial (Evolution) has been completed. Evolution II study is ongoing.

As another example, the Carillon Mitral Contour System, developed by Cardiac Dimension, Inc., Kirkland, Washington, consists of self-expandable nitinol distal and proximal anchors connected by a nitinol bridge that are placed in the great cardiac vein and proximal CS via a catheter-based system. Tension applied on the system results in cinching of the posterior periannular tissue and deflection of the posterior MA anteriorly. A feasibility study showed modestly reduced septal-lateral dimension and MR. The AMADEUS trial (CARILLON Mitral Annuloplasty Device European Union Study) using the modified CARILLON XE device (Cardiac Dimension, Inc.) has been conducted.

As a further example, the Viacor percutaneous transvenous mitral annuloplasty device, developed by Viacor, Inc., Wilmington, Massachusetts, uses nitinol rods of varying length and stiffness, delivered via a catheter to the CS.

Asymmetrical Approach: This group of devices uses the proximity of the CS to the annulus to try to reshape the mitral annulus ("MA") but in addition exert traction force on another portion of the left atrium ("LA") or right atrium, resulting in asymmetrical forces. The aim is to reduce septal-lateral dimension and decrease MR.

As an example, St. Jude Medical, based in Minneapolis, Minnesota, implanted in animal models comprising 4 helical anchors, 2 loading spacers, a tether rope, and a locking mechanism. The distal pair of anchors is delivered via the CS into the LV myocardium near the posterior leaflet scallop. The proximal pair is implanted via the right atrium into the postero-medial trigone. The 2 pairs of anchors are connected by a cable to effect cinching of the postero-medial MA. Dynamic shortening can be performed manually and reversibly, and the docking mechanism is a self-retracting, nitinol structure that maintains cinched load.

Also, the National Institutes of Health cerclage technology directs a guidewire via the CS into the first septal perforator of the great cardiac vein and, under imaging, across the myocardium to re-enter a right heart chamber. It is ensnared and exchanged for a suture and tension-fixation device.

b) Annuloplasty (Direct):

Percutaneous Mechanical Cinching Approach: This technology reshapes the MA directly without using the CS, approaching the MA from the LV or the LA side. Sutures or some other device are implanted onto the MA itself and used to directly "cinch" the MA. Devices.

As an example, the Mitralign device, developed by Mitralign, Tewksbury, Massachusetts, gains access to the annulus from the transventricular approach. Anchors are placed directly on the posterior MA and connected with a suture, creating a "purse-string" to cinch the MA.

As another example, the Accucinch Annuloplasty System, developed by Guided Delivery Systems, Santa Clara, California, uses a transventricular approach. The posterior annulus is cinched circumferentially from trigone to trigone As a further example, the Millipede system, developed by Millipede, LLC, Ann Arbor, Michigan, involves placement of a novel repositionable and retrievable annular ring with a unique attachment system via percutaneous (transseptal) or minimally invasive methods.

Percutaneous Energy-Mediated Cinching Approach: Heat energy is applied to the MA, causing scarring and shrinkage of the MA.

As an example, QuantumCor, developed by QuantumCor, Lake Forest, California, effects direct annuloplasty by use of radiofrequency energy to cause scarring and constriction of the MA. It has a loop tip that contains electrodes and thermocouples to regulate the amount of energy delivered.

Also, ReCor device, developed by ReCor, Paris, France, delivers high intensity focused ultrasound circumferentially and perpendicularly to the catheter shaft to induce tissue heating and collagen (and thus MA) shrinkage.

Hybrid Approach: An annuloplasty ring is implanted surgically and can be subsequently adjusted via transseptal access if MR recurs or worsens.

As an example, the Adjustable Annuloplasty Ring, developed by MitralSolutions, Fort Lauderdale, Florida, is implanted surgically and can be adjusted with a mechanical rotating cable.

Also, Dynamic annuloplasty Ring System, developed by MiCardia, Inc., Irving, California, is adjusted with radiofrequency energy.

3. Devices Targeting the Chordae:

Synthetic chords or sutures are implanted either from a transapical or transseptal approach and anchored onto the LV myocardium at one end, with the leaflet at the other. The length of the chord is then adjusted to achieve optimal leaflet coaptation, as exemplified by the following devices, the MitraFlex, developed by TransCardiac Therapeutics, and the NeoChord, developed by Neochord, Inc., Minnetonka, Minnesota The MitraFlex and Neochord devices place an anchor in the inner LV myocardium and another on the leaflet via a transapical approach and connect both with a synthetic "chord" trough trans-apical approach.

Babic is based on continuous suture tracks created from the LV puncture through the puncture of the target leaflet and are exteriorized via the trans-septal route. A pledget is apposed onto the exteriorized venous sutures and anchored onto the atrial side of the leaflet by retracting the guiding sutures from the epicardial end. A polymer tube is then interposed between the leaflet and free myocardial wall and secured at the epicardial surface by an adjustable knob.

4. Devices Targeting LV

A device is used to reduce the anterior-posterior dimension of the LV. This indirectly decreases the septallateral annular distance and also brings the LV papillary muscles closer to the leaflets.

The Mardil-BACE, developed by Mardil, Inc., Morrisville, North Carolina, is a silicone band that is placed around the atrioventricular groove with built-in inflatable chambre placed on the MA. This reshapes the MA for better leaflet coaptation and can be remotely adjusted after implantation. It requires a mini-thoracotomy but is implanted on a beating heart. FIM is ongoing.

5. Percutaneous MVR Technologies

At present time, different devices, such as CardiaAQ, Endovalve, Lutter, Tiara for transcatheter mitral valve replacement therapy using antegrade, transvenous, transseptal, catheter-based approach are under development. To our knowledge, they are all in the early stages of design and development and have not been approved for clinical use, and in some of them animal studies are ongoing. The challenges are formidable: the MA has an asymmetrical saddle shape, and different anchoring designs might be necessary for different MR etiologies. LV out flow obstruction might occur due to retained native valve tissue. Furthermore paravalvular leaks might also pose a problem.

In all these devices different concepts of anchoring system 20 have been developed to achieve a stabilization of the valve: anchoring below the annulus through hooks (CardiaAQ), subvalvular fixation toward mitral chord or with anchoring in the annulus with movable leaflets (Endovalve) in a nitinol self expanding tubular frame.

As an example, the CardiAQ, developed by CardiAQ Valve Technologies, Inc., Winchester, Massachusetts, prosthesis (Figure B) is delivered transseptally and locks into the inferior and superior surfaces of the mitral annulus. Animal models have been successful.

Also, the Endovalve-Herrmann prosthesis, developed by Endovalve Inc., Princeton, New Jersey, is implanted from the LA side via a right mini-thoracotomy on a beating heart, as shown in FIG. 3, The device is a foldable nitinol structure that attaches to the native valve with specially designed grippers, is fully valve sparing, and repositionable before release. Animal models have been successful, and a true percutaneous version is planned.

TABLE 2

Percutaneous Mitral Valve Regurgitation Technologies

| Site of Action | Mechanism of Action | Devices | Status |
|---|---|---|---|
| Leaflets | Leaflet Plication Edge to Edge | 1. MitraClip | RCT Currently CE mark |
|  |  | 2. Mitraflex | Preclinical |
|  | Leaflet Ablation | Thermocool | Preclinical |
|  | Leaflet Space Occupier | Percu-Pro | Phase 1 trail |
| Annulus | Indirect Annuloplasty |  |  |
|  | Coronary sinus | 1. Monarc | FIM |
|  | approach | 2. Carillon | Feasibility study |
|  | (CS reshaping) | 3. Viacor | Ongoing/completed |
|  | Asymetrical | 1. St Jude Device | Preclinical |

TABLE 2-continued

Percutaneous Mitral Valve Regurgitation Technologies

| Site of Action | Mechanism of Action | Devices | Status |
|---|---|---|---|
| | Approach | 2. NIH-Cerclage technology | |
| | Direct annuloplasty Percutaneous mechanical cinching | 1. Mitralign<br>2. Accucinch GDS<br>3. Millipede ring system | FIM<br>FIM<br>Preclinical |
| | Percutaneous energy mediated cinching | 1. QuantumCor<br>2. ReCor | Preclinical<br>Faesibility study ongoing |
| | Hybrid | 1. Mitral solutions<br>2. MiCardia | Preclinical |
| Chordal implants | Artificial chord Transapical | 1. Neochord,<br>2. MitraFlex | Preclinical |
| | Artificial chord Transapical/Transeptal | Babic | Preclinical |
| LV | LV (and MA) remodeling | Mardil-BACE | FIM |
| Percutaneous MVR Technologies | Transeptal | CardiaQ prosthesis | Preclinical |
| | Minithoracotomy | Endovalve-Herrmann prosthesis | Preclinical |
| | Transapical | Lutter prosthesis | Preclinical |
| | Transapical | Tiara prosthesis | Preclinical |

The Tiara (Neovasc, Richmond, BC, Canada) prosthesis, is a nitinol stent valve, implantable transapically. Animal models have been successful, and a true percutaneous version is planned.

As described above, the mitral valve apparatus has multiple components and displays a complex anatomical shape and structure thus limiting the number of any prevailing mitral valve repair solutions. The mitral valve technologies currently under development are actually composed of rigid valve structures, which usually distort the mitral valve plane and apparatus with unknown clinical results. Thus, there is a need for improved designs, which are conforming better to the mitral valve geometry as to keep a physiologic mitral inflow plane following valve apparatus implantation.

In regards to the percutaneous valves under development, several issues need to be considered. Balloon expandable structures depend on permanent plastic deformation induced by device expansion to a specific diameter and length. Although commonly used for treating calcified aortic stenosis, these structures are not proper fit for non-symmetrical shapes such as the mitral valve. Often resulting in para-valvular leaks following device implantation, symmetrical balloon geometries are not ideal. Although, self-expanding structures are an improvement over balloon expandable ones, a one-piece structure in a symmetrical upper and lower part of mitral valve apparatus is not ideal either. Different radial pressures might be needed against surrounding tissue potentially causing deleterious effects such as conduction system disturbances or tissue disruption. The self-positioning singular or multi-disk concept may improve upon the aforementioned limitations by securing the leaflet in between disks of different radial force, aligning a prosthetic valve to blood inflow angle and avoiding dislodgment through anchoring at the base of the mitral valve apparatus.

OBJECTS OF THE INVENTION

One of the objects of the present invention is to allow the implant of a valve concept in the region of a dysfunctional valve structure. A further object of the present invention relates to the treatment of valve insufficiency. Furthermore, it is also an object of the present invention to use the valve apparatus to replace or treat a stenosed valve.

Other and further objects and advantages of the present invention will be obvious upon an understanding of the illustrative embodiments about to be described or will be indicated in the appended claims, and various advantages not referred to herein will occur to one skilled in the art upon employment of the invention in practice.

SUMMARY OF THE INVENTION

The aforesaid and other objectives of the present invention are realized by generally providing at least one disk with self-positioning, self-centering, and self-anchoring valve apparatus. In embodiments having a plurality of disks, the apparatus may be built as an assembly of independent self-positioning, self-centering, and self-anchoring components assembled into a single valve apparatus assembly.

The disk-based valve apparatus comprises multiple components of different shapes and configurations acting as separate and independent anchoring system and allowing self-positioning and centering of a valve-housing component, as a generally median or central waist, containing the valve component.

The disk-based valve apparatus comprises one or more disks, a valve-housing component and a valve component. The one or more disks may comprise one or more notch or gap. The one or more disks may be either proximal or distal, may be either connected to each other or disconnected from each other and may either be symmetrical or have different shapes and dimensions. The disk-based valve apparatus may be self-anchoring, such as anchored by pressure from the one or more disk, or may be anchored using any anchoring mechanism such as but not limited to, needles, hooks, prongs, struts, helical configurations or any other fixation mechanisms.

The disk-based valve apparatus comprising one or more disks allows the repositioning and retrieval of the implantable valve while working on a dysfunctional valve structure.

The present invention comprises a novel and safer mechanism of deployment using a self-positioning, self-centering, and self-anchoring method. The valve apparatus, comprising one or more disks, dependently or independently interacting with each other, is maintained in place by the anchoring of the proximal and/or distal disks. Such mechanism allows the self-positioning, self-centering, ad self-anchoring of the valve, thus, maintaining the overall inflow plane of native valvular apparatus.

Furthermore, the valve apparatus comprises a double structure having a valve-housing component. The valve-housing component allows the device to be uniquely shaped and to distinguish from all other disk-based valve apparatus. Additionally, the particular shape and configuration of the distal disk ease the distal anchoring of the device. On the other end, the proximal disk facilitates the centering and stability of the valve apparatus.

The features of the present invention which are believed to be novel are set forth with particularity in the appended claims.

BRIEF DESCRIPTION OF THE DRAWINGS

The above and other objects, features and advantages of the invention will become more readily apparent from the following description, reference being made to the accompanying drawings in which:

FIG. 4D is a perspective view of a single-disk self-expanding self-positioning and self-anchoring valve apparatus in accordance with the present invention having a petal shaped proximal disk and anchoring mechanisms on the ventricular side.

FIG. 4E is a perspective transversal view of single-disk self-expanding self-positioning and self-anchoring valve apparatus in accordance with the present invention having a petal shaped proximal disk, anchoring mechanisms on the ventricular side and showing the valve component.

FIG. 6 is a perspective view of a multi-lobe self-expanding, self-positioning, and self-anchoring valve apparatus in accordance with the present invention comprising multiple independent units.

FIG. 8A is a perspective view of a single-disk self-expanding, self-positioning and self-anchoring valve apparatus in accordance with the present invention having a petal shaped proximal disk and comprising an anchoring system using hooks.

FIG. 8B is a perspective view of a caged anchoring mechanism using hooks.

FIG. 8C is a perspective view of an anchoring mechanism using hooks.

DETAILED DESCRIPTION OF THE PREFERRED EMBODIMENT

A novel self-expanding, self-positioning, and self-anchoring valve apparatus and method for the treatment of valve dysfunction will be described hereinafter. Although the invention is described in terms of specific illustrative embodiment(s), it is to be understood that the embodiment(s) described herein are by way of example only and that the scope of the invention is not intended to be limited thereby.

Figure 1:
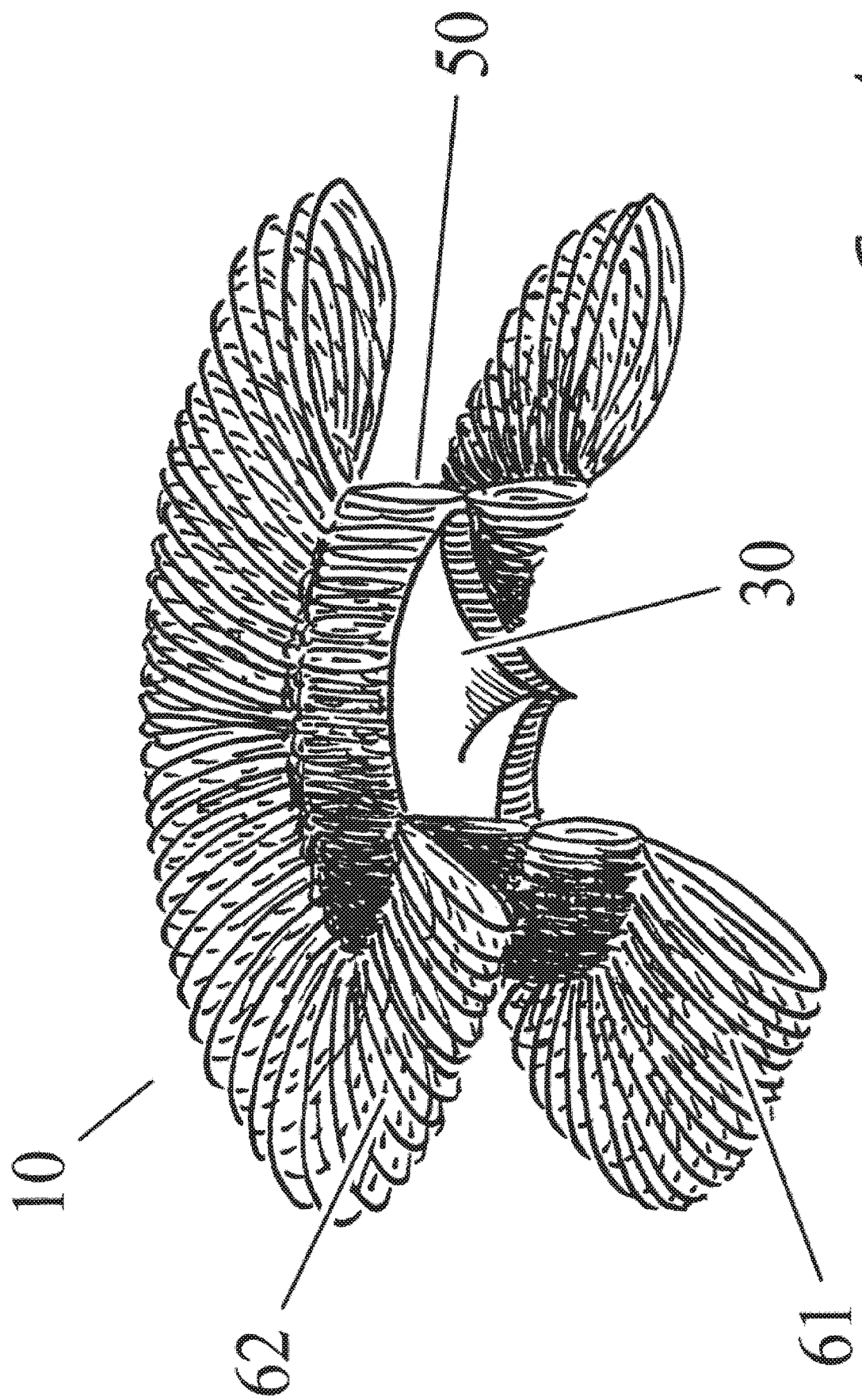
FIG. 1 presents a side view of the internal component of the valve-component housing of a multi-disk self-expanding valve apparatus in accordance with the present invention.

Referring to FIGS. 1, 5 A and 6, the apparatus 10 comprises a self-expanding, self-positioning and self-centering valve apparatus comprising at least one disk, a valve-housing component 50 referred to as central waist, an anchoring mechanism 20, and a valve component 30. In some embodiment, a cuff material 40 is inserted within the frame to direct the blood flow through the valve and not around it. Generally, the valve apparatus 10 may be made from a self-expanding material, such as, but not limited to Nitinol. The valve-housing component 50 comprises one or more self-positioning components such as different materials and different configurations to form the valve housing 50 where the valve 30 is located.

Figure 5A:
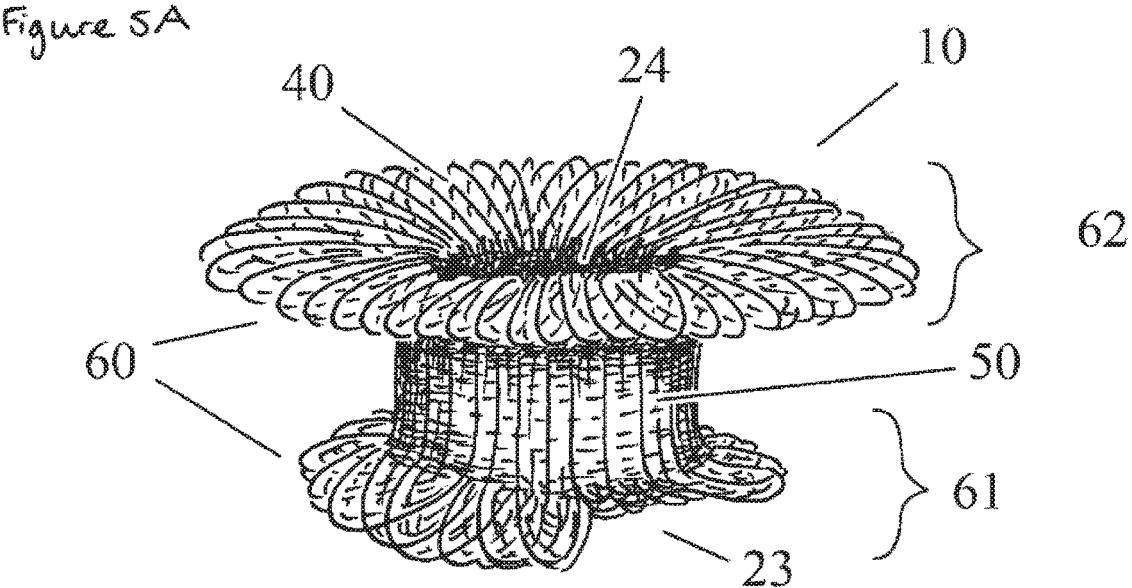
FIG. 5A is a perspective view of a multi-disk self-expanding self-positioning, and self-anchoring valve apparatus in accordance with the present invention comprising two disks being connected to each other or a single component shaped into a proximal and distal disk.

Still referring to FIGS. 1, 5A and 6, the anchoring mechanisms 20 with its proximal 21 and distal 22 components are made from materials allowing minimal deformation during heartbeat movement. Such material could be metallic or polymeric and not limited to stainless steel, nitinol, PEEK, etc. In a preferred embodiment, the disk material should be superelastic allowing a collapsed form for delivering the device and resuming its memorized configuration upon deployment at the implantation site. Materials having intrinsic memory such as Nitinol are preferable. However, any other metals and materials, such as memory-shape polymers, could also be used to manufacture or make the anchoring system 20. The valve component 30 is attached to the inner part 24 of the valve-housing component 50.

It should be noted that the disk-based, self-expanding, self-positioning, and self-anchoring valve apparatus, such as anchored by a cinching pressure force due proximal and distal disks shortening toward each other, or may be anchored using any anchoring mechanism such as but not limited to, needles, hooks, prongs, struts, helical configurations or any other fixation mechanisms.

It should be noted that within the description of the present invention, the proximal term refers to the ventricular portion while the distal term refers to the atrial portion of the valve apparatus 10. However, if valve apparatus 10 is described or installed from the atrial to the ventricular portion, the proximal term shall refer to the atrial portion and the distal term shall refer to the ventricular portion.

Typically, the anchoring system 20 comprises an atrial anchor 21 and a ventricular anchor 22. The ventricular anchor may comprise at least one notch or gap 23 to clear the aortic outflow track and the sub-valvular apparatus for instance.

Now referring to FIG. 5A, the disk-based valve apparatus 10 may be configured to adapt to a patient specific anatomical needs. Although depicted longer for representation purpose in FIG. 5A, the valve-housing component 50 is designed to exert a radial force against the mitral valve and sub-valvular apparatus, while the upper 62, and lower 61 disks are compressing the native mitral valve. These compression forces allow self-anchoring and natural positioning of the valve concept in place.

Typically, the frame of the apparatus 10 comprises a single valve-component housing 50, being covered 40 or uncovered unit or being a unitary component comprising an aperture 24 having a predetermined dimension and generally located within the central portion valve-housing 50. The frame may also comprise one or more independent units, such as the disks 60 shown in FIG. 6 forming a continuous structure. In embodiments having a frame comprising a single unit, such as the embodiment shown in FIG. 5A, all the components must be attached to allow longitudinal and axial compression of the apparatus 10.

In another embodiment, the apparatus may comprise an inner aperture 24 such as a tubular aperture, as shown in FIG. 6. In such an embodiment, the self-centering units 20 are depicted in a C-shape form allowing them to act as clips onto the mitral valve apparatus. The upper member 21 exerts a downwards self-anchoring force, while the lower member 22 exerts an upwards self-anchoring force.

Figure 2:
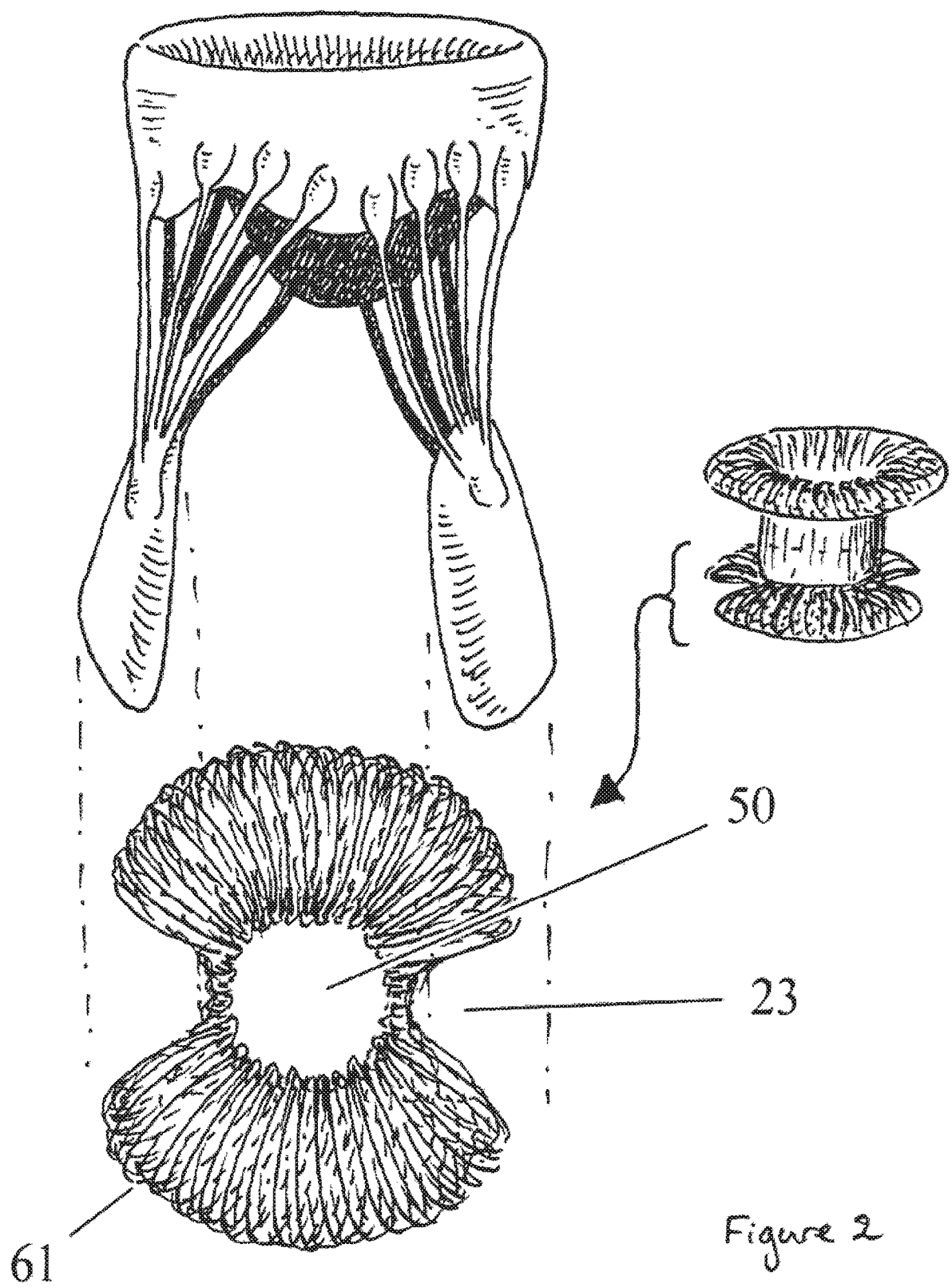
FIG. 2 depicts the view from the distal disk of a disk-based valve apparatus in accordance with the present invention in relationship with the mitral valve anatomy.
Figure 4B:
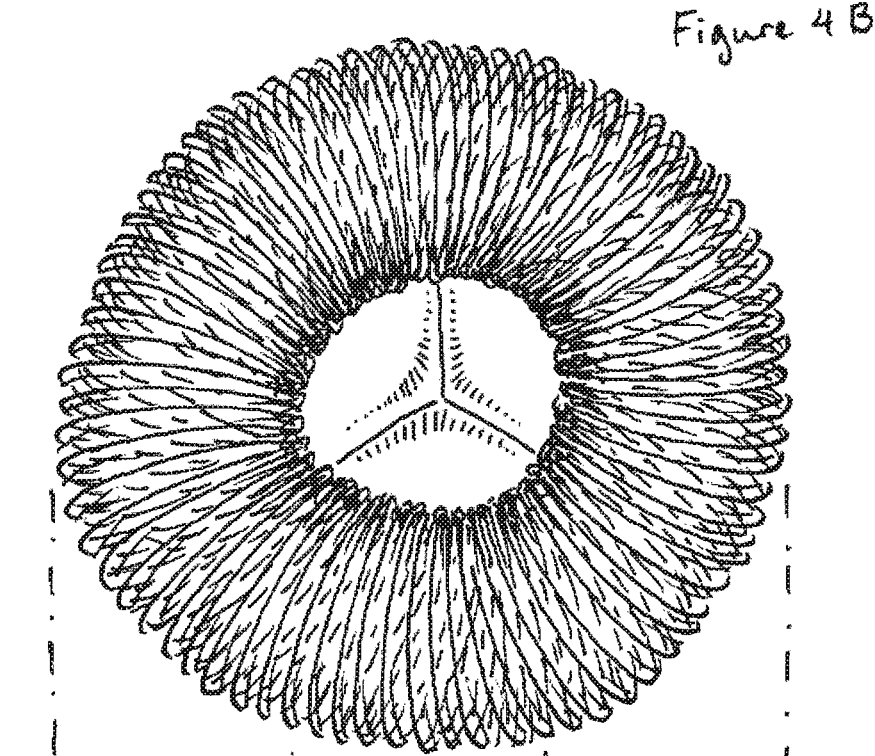
FIG. 4B is a scaled top view of a multi-disk self-expanding self-positioning and self-anchoring valve apparatus in accordance with the present invention.
Figure 4C:
FIG. 4C is a scaled side view of a multi-disk self-expanding self-positioning and self-anchoring valve apparatus in accordance with the present invention.
Figure 4A:
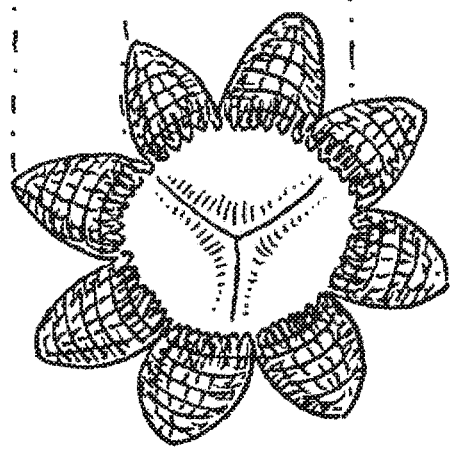
FIG. 4A is a scaled bottom view of a multi-disk self-expanding, self-positioning and self-anchoring valve apparatus in accordance with the present invention.

Now referring to FIGS. 2 and 4A, the distal disk 61 comprises an outer portion configured to allow deformation following contact with the dysfunctional valve or sub-valvular apparatus. The configuration of the distal disk 61 may vary according to the patient's anatomy. Typically, the valve-component housing 50 comprises a tunnel-like structure 24 allowing a proper positioning of the replacement valve. The valve-component housing 50 comprises a tightly woven frame in order to provide proper radial strength and longitudinal stability to the valve apparatus 10.

Figure 5B:
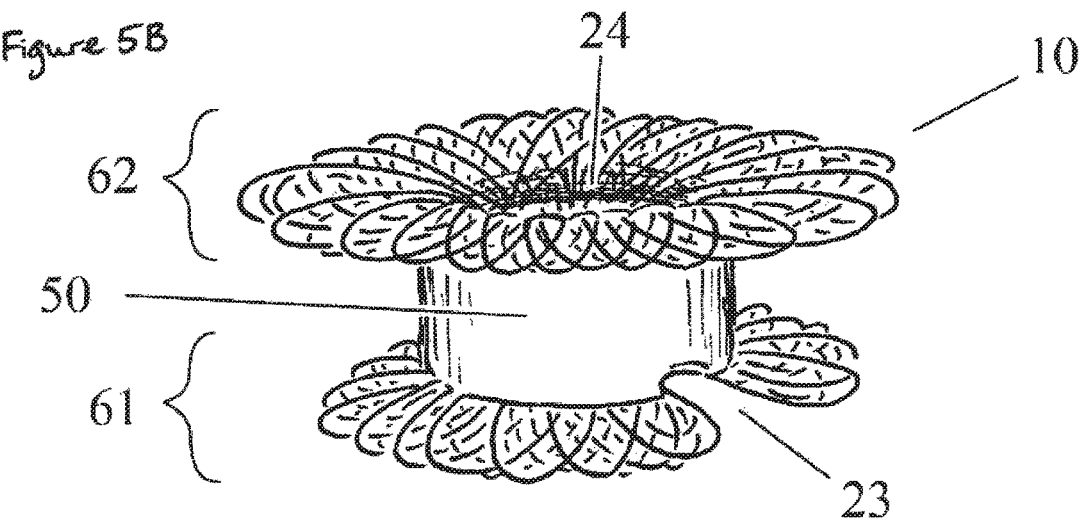
FIG. 5B is a perspective view of a multi-disk self-expanding, self-positioning, and self-anchoring apparatus in accordance with the present invention comprising independent and disconnected disks.

Referring to FIG. 5B, in another embodiment, the valve-component housing 50 may be configured as an independent unit of the valve apparatus 10, thus, allowing a plurality of mechanisms of expansion, such as balloon-based, self-based, or injectable polymer within the structure to create as expansion mechanism, to be attached to the valve apparatus 10. Such expansion mechanism may reduce or decrease the risk of device embolization, peri-valvular leak and facilitate the use of the valve apparatus 10 in the event of stenotic valvular lesions. Typically, the height of the valve-component housing 50 may range from 0.5 cm to 2.5 cm. The longitudinal diameter of the valve-component housing may range from 1.5 to 6.0 cm.

Now referring to FIGS. 5A, 5B, 6 and 7, the proximal disk 62 and distal disk 61 may have different shapes and configurations, such as, but not limited to, rounded, oval, multi-lobar or any shape covering the perimeter of the dysfunctional valve. Typically, the proximal disk 62 structure generally faces the proximal (inlet) valvular plan and the distal disk 61 is located within the distal (outlet) plane of the dysfunctional valve.

The weave of the disks is generally more open or wider than the weave of the valve-component housing 50. The disks 61 and 62 have the aim to orient the anchoring system 20 and to keep the valve-component housing 50 in its position. In other embodiments, the disks 60 maybe shaped differently. A concave disk shape may be desirable in order to allow at least one portion of a disk 60 to stay in contact with the dysfunctional valve. Additionally, other anchoring mechanisms 20, such as but not limited to, needles, hooks, prongs, struts, helical configurations or any other fixation mechanisms may be used on a disk or on the distal or proximal portion of the valve apparatus 10. It shall be noted that the proximal disk 62 may configured to have a different dimension than the distal disk 61.

Typically, the diameter of the proximal disk 62 ranges from 2.5 to 7.5 cm. In a preferred embodiment, the height of a disk 60, either distal 61 or proximal 62, shall be less than 0.5 cm.

Following the installation of the apparatus 10, the distal disk 61 is compressed by a cords and sub-valvular apparatus. At this point, the distal portion of the disk 61 remains convexly shaped and is located above the papillary muscles.

To correctly configure the distal disk 61 to the specific patient's anatomy, additional features may be required, such as hooks or anchors. In order to protect the sub-valvular apparatus and to provide enhanced valve anchoring capabilities, the distal disk 61 must be configured differently in regard to the proximal disk 62. More particularly, and as shown on FIGS. 3, 4A and 4B a distal disk 61 smaller than the proximal disk 62 may have a specific configuration, such as a "cross" or "star-like" configuration. Additionally, potential radio-opaque markers may be installed in order to allow the anchoring of the distal disk underneath the sub-valvular apparatus.

Typically, the diameter of the distal disk 61 ranges from 2.5 to 7.5 cm. However, the height of the distal disk 61 should vary according to the dimension and shape of the sub-valvular anatomy. When implanted, the distal disk 61 may comprise one or more additional sub-valvular anchoring structure 20, such structure 20 allowing better apposition and fixation to the dysfunctional valve.

FIG. 4C is a scaled side view of a multi-disk self-expanding self-positioning and self-anchoring valve apparatus in accordance with the present invention. FIG. 4D is a perspective view of a single-disk self-expanding self-positioning and self-anchoring valve apparatus in accordance with the present invention having a petal shaped proximal disk and anchoring mechanisms on the ventricular side. As shown in FIG. 4D, the proximal disk includes petals disposed in an overlapping arrangement. FIG. 4E is a perspective transversal view of single-disk self-expanding self-positioning and self-anchoring valve apparatus in accordance with the present invention having a petal shaped proximal disk, anchoring mechanisms on the ventricular side and showing the valve component. As shown in FIG. 4E, the proximal disk includes petals disposed in an overlapping arrangement. FIGS. 5A and 5B also show disk portions with petals disposed in overlapping arrangements.

The valve apparatus 10 may be completely or partially covered or laminated using different and/or independent material. Such covering may be installed or placed outside or inside of the structural cage 40 of the valve apparatus 10. The material use to cover or laminate the frame may be interwoven with the frame.

Any type of valve component 30, such as biological valve or synthetic valve, may be used as a valve component 30 of the valve apparatus 10. A biological valve graft or synthetic valve may be sutured to the valve-component housing 50 of the anchoring mechanism 20. It should be appreciated by the one skilled in the art that any other mean of attachment of the valve component 30 to the valve-component housing 50 may be used. Typically, the valve component 30 is made of biological material or of synthetic tissues. A valve component 30 made from biological material may be homo or hetero graft.

The valve component 30 may comprise two or more leaflets, wherein such leaflets are self-sealable due to the pressure gradient or difference between the atrium and the ventricle.

A delivery system comprises a loading system, a catheter, a short and a long pusher wire. The catheter may be steerable in order to properly orient the system through the valve during the release phase. The delivery system is loaded on the pusher wire with an attachment method such as a screw or a bayonet. Once loaded, the delivery system is inserted and pushed to the tip of the catheter positioned in the ventricle. Following the insertion of the delivery system, the distal portion of the system is released in the ventricle and the catheter is retrieved to the atrio-ventricular plan. Consequently, the valve-component housing 50 is released and followed by the proximal portion.

In a preferred embodiment, such as shown in FIG. 5A, a valve apparatus 10 comprising a single unit may be hollowed. The valve apparatus comprises a valve component in a generally central portion 50 and two disks 60, a proximal 62 and a distal 61. The apparatus may comprise at least one separate anchoring mechanism 20, as shown by the disks 21 and 22 but may be anchored using the pressure of the disks 60. Once the distal disk 61 is distally inserted within the patient's dysfunctional valve, the distal disk 61 is released in a distal orientation in regard to the sub-valvular apparatus. Upon deformation of the distal disk 61, the entire valve apparatus 10 is pulled back into the plane of the dysfunctional valve in order to position the valve component 30 located in the valve-component housing 50, as shown in FIGS. 3, 4, 5A and 5B. Once the first disk 61 positioned, the second disk 62 is released in order to secure the apparatus 10 in place. This configuration may be changed or adapted according to the route of insertion, such as anterograde versus retrograde or percutaneous versus trans-apical versus trans-atrial.

In another embodiment, the valve apparatus 10, as a single unit, comprises a valve component 30 generally located in the valve-component housing 50 of the apparatus 10 and two disks 60, a proximal 62 and a distal 61. The apparatus may comprise at least one separate anchoring mechanism 20, as shown by the disks 21 and 22 but may be anchored using the pressure of the disks 60. When the insertion of the distal disk 61 is completed within the patient's dysfunctional valve, the distal disk 61 is released in a distal orientation in regard to the sub-valvular apparatus. The distal disk 61 comprises at least one additional anchoring structures 20, such as but not limited to needles, hooks, prongs, struts, helical configurations or any other fixation mechanisms. The at least one anchoring structure 20 allows the sub-valvular anchoring and positioning of the distal disk 61. Upon deformation of the distal disk 61. The valve apparatus 10 is pulled back into the plane of the patient's dysfunctional valve in order to position the valve component 30 located in the valve-component housing 50 of the apparatus 10. Once the distal disk 61 positioned, the second disk 62 is released in order to secure the entire cage in place. The configuration of this embodiment may be changed or adapted according to the route of insertion, such as anterograde versus retrograde or percutaneous versus trans-apical versus trans-atrial.

In a further second embodiment, which is similar to the embodiment described above, the valve apparatus 10 comprises a single distal anchoring disk 61. When the insertion of the apparatus 10 is completed within the patient's dysfunctional valve, a distal disk 61 is released. At this point, the distal disk 61 is partially deformed and the valve-component housing 50 is positioned at the level of the dysfunctional valve plane. Then, the proximal segment of the apparatus 10 is fully released to complete the positioning of the valve apparatus 10.

In a further third embodiment, which is based on the further second embodiment, the valve apparatus 10 comprises a single distal anchoring disk 61 and a smaller and shorter proximal disk 62. When the insertion of the valve apparatus 10 is completed within the patient's dysfunctional valve, the distal disk 61 is released. At this point, the distal disk 61 is partially deformed and the valve-component housing 50 is positioned at the level of the dysfunctional valve plane. Then, as the proximal segment 62 of the valve apparatus 10 is fully released, the positioning of the valve apparatus 10 is completed.

In a further fourth embodiment, as shown in FIG. 6, a valve apparatus 10 comprises a plurality of independent units, which may be hollowed, a valve component 30 generally located in the central portion 50 and at least two separate anchoring systems 20 or disks 60. When the insertion of the valve apparatus 10 is completed, the distal disks 61 are released. Even if not required, each distal disk 61 may comprise one or more additional anchoring structures allowing the sub-valvular to be anchored and positioned in regards to the distal disk 61. Upon deformation of the distal disk 61, the apparatus 10 is pulled back into the plane of the dysfunctional valve in order to position the valve component 30 located in the valve-component housing 50. The valve apparatus 10 is positioned into an expandable structure, such as a balloon. The expandable structure may be deployed following initial positioning of the valve apparatus 10. Once positioned, a second disk 62 is released in order to secure the entire apparatus 10 in place. The configuration of this embodiment may be changed or adapted according to the route of insertion, such as anterograde versus retrograde or percutaneous versus trans-apical versus trans-atrial.

Figure 7:
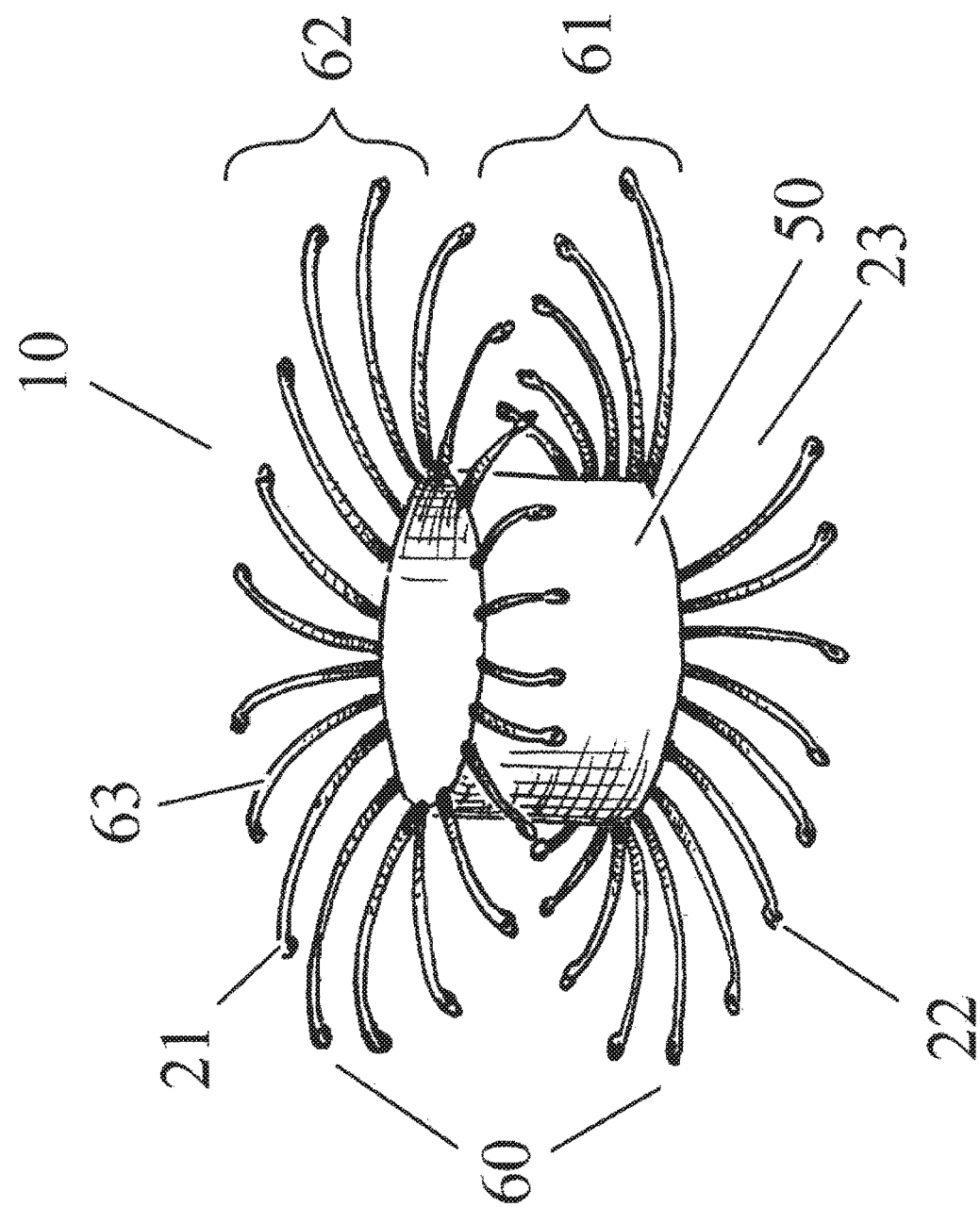
FIG. 7 is a perspective view of a single-disk with multi-lobes self-expanding, self-positioning, and self-anchoring valve apparatus in accordance with the present invention comprising wiring with teardrops end as anchor system.

In a further fifth embodiment, as shown in FIG. 7, a valve apparatus 10 comprises a plurality of wires 63 distributed in a way to form one or more disks 60, either distal 61 or proximal 62, and a valve component 30 generally located in the central portion 50. Each wire 63 may comprise an anchoring mechanism such as a hook or needle. When the insertion of the valve apparatus 10 is completed, the distal disk 61 is released. Upon deformation of the distal disk 61, the apparatus 10 is pulled back into the plane of the dysfunctional valve in order to position the valve component 30 located in the valve-component housing 50. Once positioned, a second disk 62 is released in order to secure the entire apparatus 10 in place. The configuration of this embodiment may be changed or adapted according to the route of insertion, such as anterograde versus retrograde or percutaneous versus trans-apical versus trans-atrial.

Figure 3:
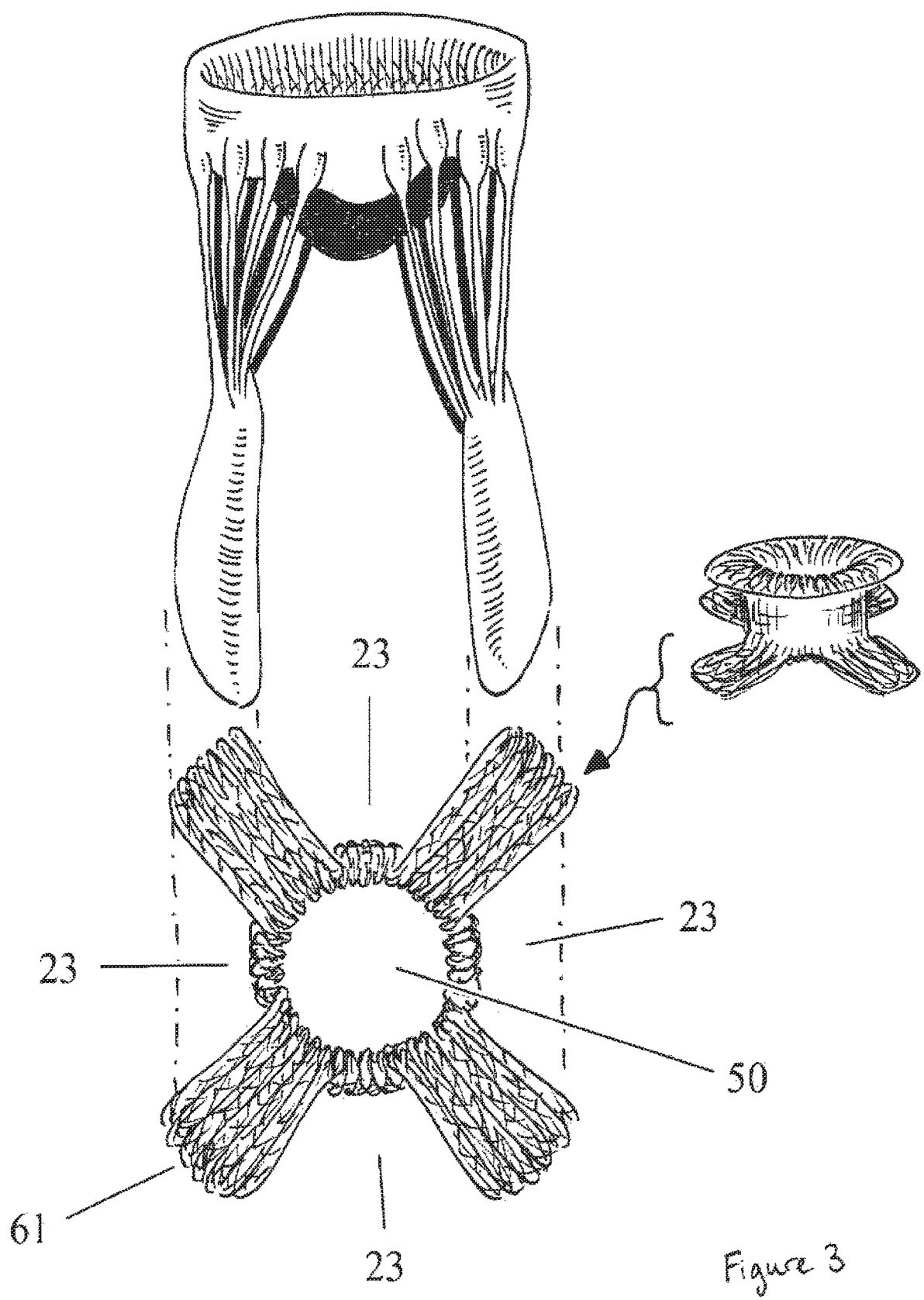
FIG. 3 depicts the view from the distal disk of a disk-based valve apparatus in accordance with the present invention, the distal disk having a cross-like shape and being shown in relationship with the mitral valve anatomy.

In a further sixth embodiment, as depicted in FIG. 3, a cage device comprises a single unit, wherein such unit may be hollowed, a valve component 30 generally located in the apparatus central portion 50 and at least two separate anchoring systems 20 or disks 60. Additionally, the distal anchoring system 20 may comprise two or more disks 60, referred as a multi-lobar disk. In this embodiment, the preferred shape or configuration of the distal disk is a cross-like or "star-like" structure. When the insertion of the entire device distally located in regard to the patient's dysfunctional valve is completed, the distal multi-lobar disk is distally released, in regard to the sub-valvular apparatus, between the junction chordae tendinea/papillary muscles in order to keep the subvalvular apparatus intact and to provide an optimal anchoring to the system. The distal disks 61 may comprise at least one additional anchoring structure 20, such as but not limited to needles, hooks, prongs, struts, helical configurations or any other fixation mechanisms. The anchoring structure 20 allows the sub-valvular anchoring and positioning of the distal disks 61. The addition of markers may be required to orient the apparatus 10 during the deployment of the apparatus 10. Upon deformation of the distal disks 61, the entire cage structure 40 is pulled back into the plane of the dysfunctional valve in order to position the new valve located in the valve-component housing 50. Once positioned, the proximal disk 62 is released in order to secure the entire cage in place. The configuration of this embodiment may be changed or adapted according to the route of insertion, such as anterograde versus retrograde or percutaneous versus trans-apical versus trans-atrial.

While illustrative and presently preferred embodiment(s) of the invention have been described in detail hereinabove, it is to be understood that the inventive concepts may be otherwise variously embodied and employed and that the appended claims are intended to be construed to include such variations except insofar as limited by the prior art.

The invention claimed is:

1. A mitral valve prosthesis having a constrained shape and an expanded shape, the mitral valve prosthesis comprising:
    a replacement valve attached to a valve-component housing; and
    an anchor, the anchor including:
    a proximal atrial portion adapted and configured to self-expand from the constrained shape into the expanded shape,
        wherein the proximal atrial portion comprises a plurality of wires of shape memory material, and
        wherein the proximal atrial portion flares radially outwardly;
    a distal portion adapted and configured to self-expand from the constrained shape to the expanded shape, wherein the replacement valve allows blood to flow from the proximal atrial portion toward the distal portion but prevents blood from flowing from the distal portion toward the proximal atrial portion; and
    a plurality of hooks extending from the distal portion and extending in a proximal direction to prevent dislodgment of the mitral valve prosthesis into a left atrium;
    wherein the valve-component housing is unit of the mitral valve prosthesis that is independent of the anchor of the mitral valve prosthesis and includes a cylindrical central portion connected to the distal portion prior to implantation and extending proximally, wherein when in the expanded shape the cylindrical central portion has a height that is greater than a height of the proximal atrial portion,
    wherein the mitral valve prosthesis is rotationally symmetric about a plurality of degrees of rotational symmetry such that the mitral valve prosthesis is adapted for implantation in any rotational orientation corresponding to the plurality of degrees of rotational symmetry relative to a native mitral valve.

2. The mitral valve prosthesis of claim 1, wherein the distal portion comprises a plurality of wire petals of shape memory material.

3. The mitral valve prosthesis of claim 2, wherein the plurality of wire petals of the distal portion are disposed in an overlapping arrangement.

4. The mitral valve prosthesis of claim 1, wherein when in the expanded shape the central portion has a diameter smaller than diameters of the proximal atrial portion and the distal portion in their expanded shapes.

5. The mitral valve prosthesis of claim 1, wherein the plurality of wires of the proximal atrial portion are a plurality of wire petals disposed in an overlapping arrangement and formed of shape memory material.

6. The mitral valve prosthesis of claim 5, wherein when in the expanded shape the central portion has a diameter smaller than diameters of the proximal portion and the distal portion in their expanded shapes.

7. The mitral valve prosthesis of claim 1, wherein the cylindrical central portion is disposed between, and connected to, the proximal atrial portion and the distal portion, the central portion being adapted to self-expand to move the proximal atrial portion and the distal portion toward each other to compress native cardiac tissue between them.

\* \* \* \* \*